(12) United States Patent
Gao et al.

(10) Patent No.: US 12,365,761 B2
(45) Date of Patent: Jul. 22, 2025

(54) BIODEGRADABLE ULTRA-PH SENSITIVE POLYMERS

(71) Applicant: The Board of Regents of The University of Texas System, Austin, TX (US)

(72) Inventors: Jinming Gao, Dallas, TX (US); Xu Wang, Dallas, TX (US); Houliang Tang, Dallas, TX (US); Wei Li, Dallas, TX (US); Jonathan Wilhelm, Dallas, TX (US); Baran Sumer, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 575 days.

(21) Appl. No.: 17/620,570

(22) PCT Filed: Jun. 22, 2020

(86) PCT No.: PCT/US2020/038915
§ 371 (c)(1),
(2) Date: Dec. 17, 2021

(87) PCT Pub. No.: WO2020/263733
PCT Pub. Date: Dec. 30, 2020

(65) Prior Publication Data
US 2022/0380534 A1 Dec. 1, 2022

Related U.S. Application Data

(60) Provisional application No. 62/865,187, filed on Jun. 22, 2019.

(51) Int. Cl.
*C08G 64/30* (2006.01)
*A61K 9/107* (2006.01)
(Continued)

(52) U.S. Cl.
CPC .......... *C08G 65/3332* (2013.01); *A61K 9/107* (2013.01); *A61P 35/00* (2018.01); *C08G 65/3342* (2013.01); *A61K 9/0019* (2013.01)

(58) Field of Classification Search
CPC ...... C08G 64/30; C08G 64/183; C08G 65/48; A61K 47/34
See application file for complete search history.

(56) References Cited

U.S. PATENT DOCUMENTS

2003/0199090 A1  10/2003  Monahan et al.
2005/0113531 A1   5/2005  Chang et al.
(Continued)

FOREIGN PATENT DOCUMENTS

CN    109069440      12/2018
JP    2017-526753     9/2017
(Continued)

OTHER PUBLICATIONS

Tempelaar et al. Organocatalytic Synthesis and Postpolymerization Functionalization of Allyl-Functional Poly(carbonate)s. Mar. 15, 2011. Macromolecules. vol. 44. Issue 7. pp. 2084-2091. <https://doi.org/10.1021/ma102882v>. (Year: 2011).*
(Continued)

*Primary Examiner* — Mark S Kaucher
(74) *Attorney, Agent, or Firm* — Parker Highlander PLLC

(57) ABSTRACT

The present disclosure relates to degradable polymers which contain a hydrophobic and hydrophilic segment which is sensitive to pH. In some aspects, the polymers form a micelle which is sensitive to pH and have backbones which are capable of undergoing degradation in vivo. In some aspects, the disclosure also provides methods of using these degradable polymers for the delivery of a drug.

14 Claims, 16 Drawing Sheets

Specification includes a Sequence Listing.

(51) Int. Cl.
*A61P 35/00* (2006.01)
*C08G 65/333* (2006.01)
*C08G 65/334* (2006.01)
*A61K 9/00* (2006.01)

(56) References Cited

U.S. PATENT DOCUMENTS

| | | |
|---|---|---|
| 2005/0201972 A1 | 9/2005 | Seo et al. |
| 2009/0247666 A1 | 10/2009 | Yu et al. |
| 2011/0152167 A1 | 6/2011 | Hedrick et al. |
| 2014/0296462 A1 | 10/2014 | Mahanthappa et al. |
| 2018/0369424 A1 | 12/2018 | Gao et al. |
| 2019/0060446 A1 | 2/2019 | Gao et al. |
| 2019/0167584 A1* | 6/2019 | Boday .................. C08G 83/008 |

FOREIGN PATENT DOCUMENTS

| | | | |
|---|---|---|---|
| WO | WO 2015-188157 | 12/2015 | |
| WO | WO-2017151922 A1 * | 9/2017 | ......... A61K 39/0011 |
| WO | WO 2019-111121 | 6/2019 | |

OTHER PUBLICATIONS

Baccala et al., "TLR-dependent and TLR-independent pathways of type I interferon induction in systemic autoimmunity," Nat. Med., 13(5):543-551, 2007.
Barber, "STING: infection, inflammation and cancer," Nat. Rev. Immunol., 15(12):760-770, 2015.
Blum et al., "Stimuli-responsive nanomaterials for biomedical applications," J. Am. Chem. Soc., 137:2140-2154, 2015.
Casey et al., "Sensors and regulators of intracellular pH," Nat. Rev. Mol. Cell Bio., 11:50-61, 2010.
Extended European Search Report issued in European Application No. 20831733.9, mailed Jun. 21, 2023.
Fuertes et al., "Type I interferon response and innate immune sensing of cancer," Trends Immunol., 34(2):67-73, 2013.
Gerweck and Seetharaman, "Cellular pH gradient in tumor versus normal tissue: potential exploitation for the treatment of cancer," Cancer Res., 56(6):1194-1198, 1996.
Hao et al., "Rapid Synthesis of a Lipocationic Polyester Library via Ring-Opening Polymerization of Functional Valerolactones for Efficacious siRNA Delivery," J. Am. Chem. Soc., 137(29):9206-9209, 2015.
Hu et al., "Synthesis and characterization of amphiphilic block copolymers with allyl side-groups," J. Polym. Sci. Part A: Polym. Chem., 45(23):5518-5528, 2007.
Ishikawa and Barber, "Sting is an endoplasmic reticulum adaptor that facilitates innate immune signalling," Nature, 455(7213):674-678, 2008.
Karmegam et al., "Biodegradable aliphatic polyesters for drug delivery," *Material Matters*, 12(2):1-7, 2017.
Li et al., "Molecular basis of cooperativity in pH-triggered supramolecular self-assembly," Nat. Commun., 7:13214, 2016.
Luo et al., "A Sting-activating nanovaccine for cancer immunotherapy," Nat. Nanotechnol., 12(7):648-654, 2017.
Luo et al., "Synergistic STING activation by PC7A nanovaccine and ionizing radiation improves cancer immunotherapy," *Journal of Controlled Release*, 300:154-160, 2019.
Moitra et al., "Efficacious anticancer drug delivery mediated by a pH-sensitive self-assembly of a conserved tripeptide derived from tyrosine kinase NGF receptor," Angew. Chem. Int. Ed. Engl., 53(4):1113-1117, 2014.
Office Action issued in Chinese Application No. 202080058689.7, mailed Dec. 15, 2023, and English translation thereof.
PCT International Preliminary Report on Patentability issued in International Application No. PCT/US2020/038915, mailed Jan. 6, 2022.
PCT International Search Report and Written Opinion issued in International Application No. PCT/US2020/038915, mailed Sep. 16, 2020.
Reineke, "Stimuli-Responsive Polymers for Biological Detection and Delivery," ACS Macro Lett., 5:14-18, 2016.
Sethuraman et al., "TAT peptide-based micelle system for potential active targeting of anti-cancer agents to acidic solid tumors," *Journal of Controlled Release*, 118(2):216-224, 2007.
Torchilin, "Multifunctional, stimuli-sensitive nanoparticulate systems for drug delivery," Nat. Rev. Drug Discovery, 13(11):813-827, 2014.
Wang et al., "A nanobuffer reporter library for fine-scale imaging and perturbation of endocytic organelles," Nat. Commun., 6:8524, 2015.
Wang et al., "A nanoparticle-based strategy for the imaging of a broad range of tumours by nonlinear amplification of microenvironment signals," Nat. Mater., 13(2):204-212, 2014.
Wang et al., "A Redox-Activatable Fluorescent Sensor for the High-Throughput Quantification of Cytosolic Delivery of Macromolecules," Angew. Chem. Int. Ed., 56:1319-1323, 2017.
Wang et al., "Investigation of endosome and lysosome biology by ultra pH-sensitive nanoprobes," Adv. Drug Delivery Rev., 113:87-96, 2017.
Yang et al., "Stimuli responsive drug delivery systems based on nano-graphene for cancer therapy," Adv. Drug Delivery Rev., 105(Pt B):228-241, 2016.
Zhang et al., "Tunable pH-Responsive Polymeric Micelle for Cancer Treatment," ACS Macro Lett., 4:620-623, 2015.
Zhao et al., "A transistor-like pH nanoprobe for tumour detection and image-guided surgery," Nat. Biomed. Eng., 1:0006, 2017.
Zhou et al., "Tunable, ultrasensitive pH-responsive nanoparticles targeting specific endocytic organelles in living cells," Angew. Chem. Int. Ed., 50:6109-6114, 2011.
Zitvogel et al., "Type I interferons in anticancer immunity," Nat. Rev. Immunol., 15:405-414, 2015.
Cho et al., "A Vinyl Ether-Functional Polycarbonate as a Template for Multiple Postpolymerization Modifications," *Macromolecules*, 51(9):3233-3242, 2018.
Lee et al., "pH-Tunable Thermoresponsive PEO-Based Functional Polymers with Pendant Amine Groups," *ACS Macroletters*, 5(12):1391-1396, 2016.
Office Action issued in Singaporean Application No. 11202114155W, mailed Jan. 16, 2024.
Yu et al., "Facile construction of near-monodisperse and dual responsive polycarbonate mixed micelles with the ability of pH-induced charge reversal for intracellular delivery of antitumor drugs," *J Mater Chem B.*, 4(36):6081-6093, 2016.
Yue et al., "Modular Functionalization of Amphiphilic Block Copolymers via Radical-Mediated Thiol-Ene Reaction," *Macromolecules*, 43(23):9645-9654, 2010.
Office Action issued in Korean Application No. 10-2022-7001363, mailed Dec. 25, 2024, and English translation thereof.

* cited by examiner

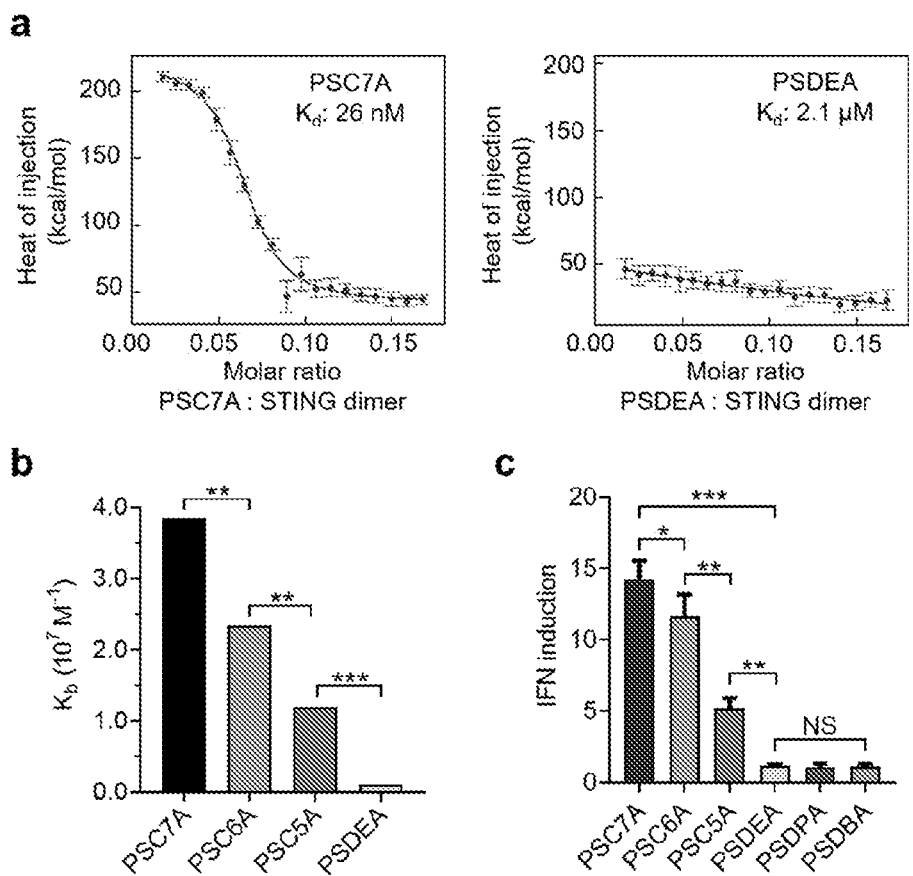
FIGS. 12A-C

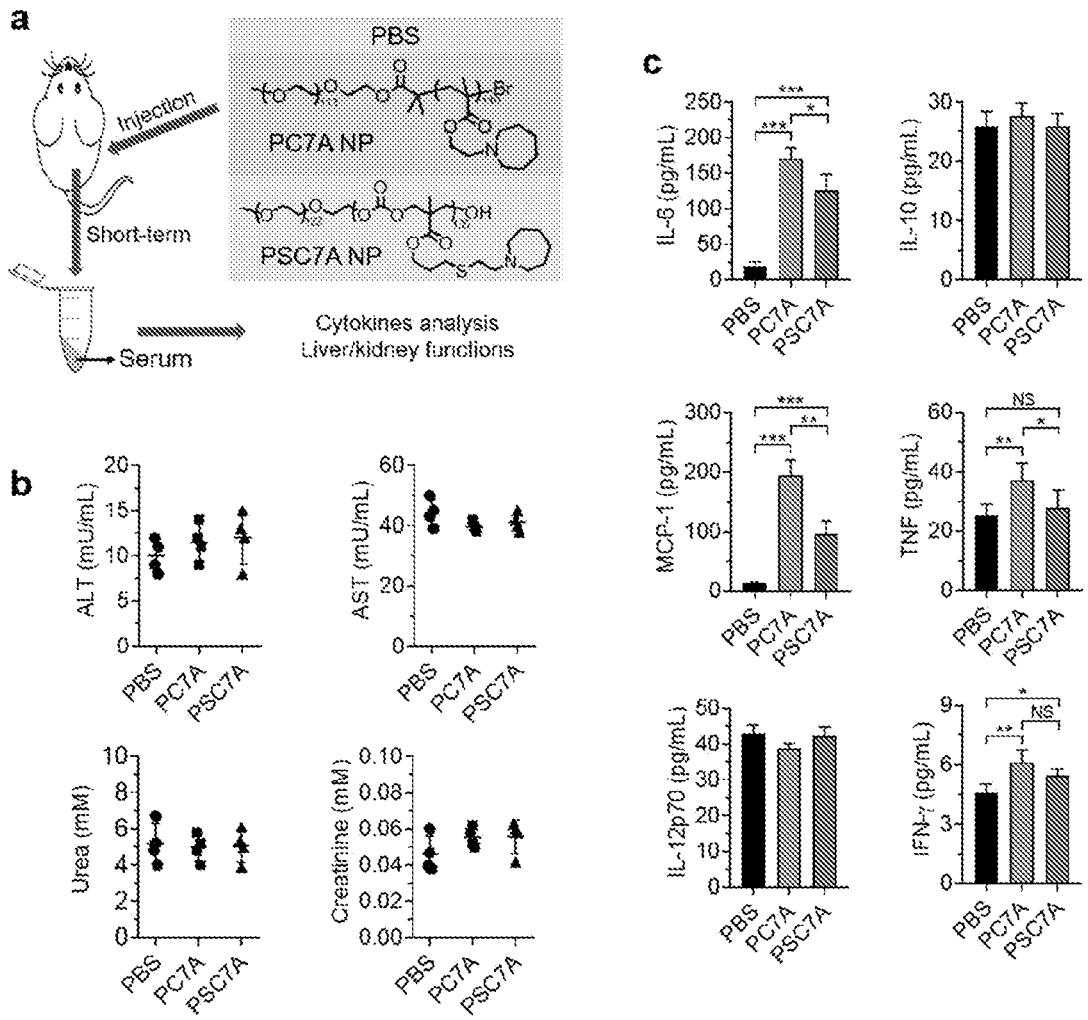
FIGS. 15A-C

FIGS. 17A-D

BIODEGRADABLE ULTRA-PH SENSITIVE POLYMERS

This application is a national phase application under 35 U.S.C. § 371 of International Application No. PCT/US2020/038915, filed Jun. 22, 2020, which claims priority to U.S. Provisional Application No. 62/865,187, dated Jun. 22, 2019, the entire contents of each of which are hereby incorporated by reference.

This invention was made with government support under Grant Number R01 CA216839 and U01 CA218422 awarded by the National Institutes of Health. The government has certain rights in the invention.

BACKGROUND

1. Field

The present disclosure relates generally to the fields of molecular and cellular biology, drug delivery, and nanotechnology. More particularly, it relates to degradable polymers which may be used for the delivery of a therapeutic agent.

2. Description of Related Art

Stimuli-responsive materials have rapidly advanced into a broad range of medical applications in recent years (Blum et al., 2015; Reineke, 2016; Torchilin, 2014; Yang et al., 2016). A variety of pH-sensitive polymers and nanoparticles have been designed and investigated for tumor imaging and drug delivery applications (Moitra et al., 2013; Moitra et al., 2014; Zhang et al., 2015). For many biological applications, the difference between organelle pH at different maturation states such as early endosomes vs. late endosomes or between tumor microenvironment and normal tissue pH is small including pH differences as small as less than 1 pH unit, (Casey et al., 2009; Gerweck and Seetharaman, 1996) which makes it challenging for conventional small molecular or polymeric pH sensors to differentiate. In recent years, a series of ultra-pH sensitive (UPS) copolymers with a binary response to the environmental pH have been developed. Ionizable residues such as tertiary amines with different hydrophobic substituents were introduced onto the backbone of poly(methyl methacrylate) (PMMA) polymer. Hydrophobic micellization was theorized to contribute to the sharp pH response (e.g., fluorescence on/off activation within 0.25 pH unit). The resulting transistor-like nanoparticles have shown improved precision in multiple biological applications, including tumor imaging and surgery (Zhou et al., 2011a; Zhou et al., 2011b; Wang et al., 2013; Zhao et al., 2016), image and perturbation of endocytic organelles and lysosome catabolism (Wang et al., 2015; Wang et al., 2017), and nanovaccines for cancer immunotherapy (Wang et al., 2016; Luo et al., 2017).

As noted above, the current UPS copolymers are synthesized using the non-degradable PMMA polymer backbones which hampers the ability of these polymers to be cleared from the body. For certain medical applications such as cancer surgery, the frequency of usage (i.e., single injection prior to surgery) and low toxicity of imaging agent (e.g., indocyanine green) render the PMMA design safe for human use. However, in other applications where repeated injections are necessary such as drug or gene delivery, the PMMA design may lead to excessive material accumulation in the body and limit the safety of prolonged clinical use of these UPS copolymers.

Therefore, there remains a need to develop and prepare polymer systems which may be used to use to deliver therapeutic agents that are able to be degraded in vivo.

SUMMARY

In some aspects, the present disclosure provides polymers of the formula:

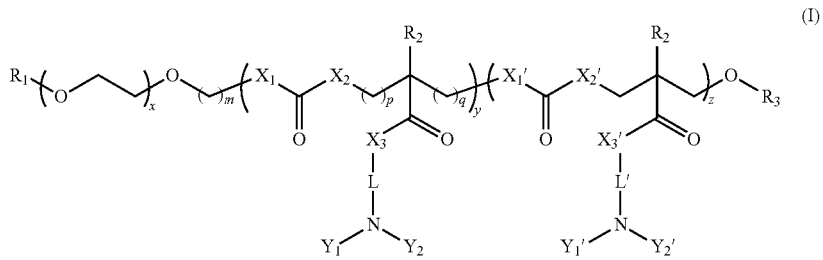

wherein:
  $R_1$ is hydrogen, alkyl$_{(C \le 8)}$, substituted alkyl$_{(C \le 8)}$, or a thiol reactive group;
  m is an integer from 1 to 8;
  p and q are each independently 1, 2, or 3;
  x is an integer from 10 to 200;
  y is an integer from 20 to 200;
  z is an integer from 0 to 200;
  wherein the monomer of either y or z is randomly distributed in the polymer;
  $X_1$, $X_2$, $X_1'$, and $X_2'$ are each independently O or $NR_a$, wherein:
    $R_a$ is alkyl$_{(C \le 6)}$ or substituted alkyl$_{(C \le 6)}$;
  $R_2$ and $R_2'$ are each independently hydrogen, alkyl$_{(C \le 8)}$, or substituted alkyl$_{(C \le 8)}$;
  $R_3$ is hydrogen, alkyl$_{(C \le 8)}$, or substituted alkyl$_{(C \le 8)}$;
  $X_3$ and $X_3'$ are each independently O or $NR_b$, wherein:
    $R_b$ is hydrogen, alkyl$_{(C \le 6)}$, or substituted alkyl$_{(C \le 6)}$;
  L and L' are each independently a group of the formula:

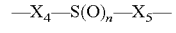

wherein:
    n is 0, 1, or 2; and
    $X_4$ and $X_5$ are each independently alkanediyl$_{(C \le 8)}$ or substituted alkanediyl$_{(C \le 8)}$; and
  $Y_1$, $Y_2$, $Y_1'$, and $Y_2'$ are each independently alkyl$_{(C \le 12)}$, substituted alkyl$_{(C \le 12)}$, alkenyl$_{(C \le 12)}$, or substituted alkenyl$_{(C \le 12)}$; or $Y_1$ and $Y_2$ or $Y_1'$ and $Y_2'$ are taken together and are alkanediyl$_{(C \le 12)}$, alkenediyl$_{(C \le 12)}$, or a substituted version of either group;
or a pharmaceutically acceptable salt thereof.

In some embodiments, the polymers are further defined as:

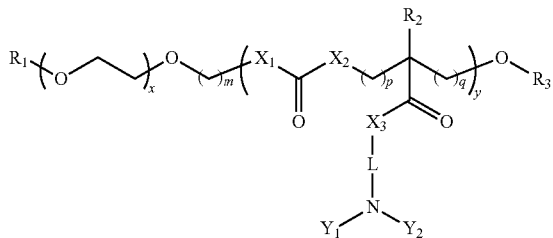
(II)

wherein:
$R_1$ is hydrogen, alkyl$_{(C\leq8)}$, substituted alkyl$_{(C\leq8)}$, or a thiol reactive group;
m is an integer from 1 to 8;
p and q are each independently 1, 2, or 3;
x is an integer from 10 to 200;
y is an integer from 20 to 200;
$X_1$ and $X_2$ are each O or NR$_a$, wherein:
$R_a$ is hydrogen, alkyl$_{(C\leq6)}$, or substituted alkyl$_{(C\leq6)}$;
$R_2$ is hydrogen, alkyl$_{(C\leq8)}$, or substituted alkyl$_{(C\leq8)}$;
$R_3$ is hydrogen, alkyl$_{(C\leq8)}$, or substituted alkyl$_{(C\leq8)}$;
$X_3$ is O or NR$_b$, wherein:
$R_b$ is hydrogen, alkyl$_{(C\leq6)}$, or substituted alkyl$_{(C\leq6)}$;
L is a group of the formula:

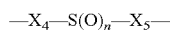

wherein:
n is 0, 1, or 2; and
$X_4$ and $X_5$ are each independently alkanediyl$_{(C\leq8)}$ or substituted alkanediyl$_{(C\leq8)}$; and
$Y_1$ and $Y_2$ are each independently alkyl$_{(C\leq12)}$, substituted alkyl$_{(C\leq12)}$, alkenyl$_{(C\leq12)}$, or substituted alkenyl$_{(C\leq12)}$; or $Y_1$ and $Y_2$ are taken together and are alkanediyl$_{(C\leq12)}$, alkenediyl$_{(C\leq12)}$, or a substituted version of either group;
or a pharmaceutically acceptable salt thereof.

In some embodiments, the polymers are further defined as:

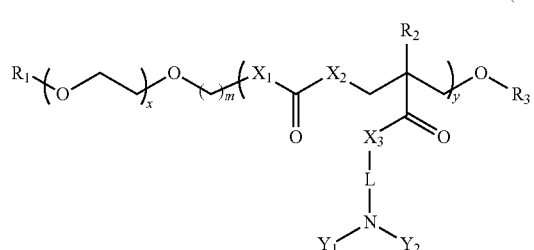
(III)

wherein:
$R_1$ is hydrogen, alkyl$_{(C\leq8)}$, substituted alkyl$_{(C\leq8)}$, or a thiol reactive group;
m is an integer from 1 to 8;
x is an integer from 10 to 200;
y is an integer from 20 to 200;
$X_1$ and $X_2$ are each O or NR$_a$, wherein:
$R_a$ is hydrogen, alkyl$_{(C\leq6)}$, or substituted alkyl$_{(C\leq6)}$;
$R_2$ is hydrogen, alkyl$_{(C\leq8)}$, or substituted alkyl$_{(C\leq8)}$;
$R_3$ is hydrogen, alkyl$_{(C\leq8)}$, or substituted alkyl$_{(C\leq8)}$;
$X_3$ is O or NR$_b$, wherein:
$R_b$ is hydrogen, alkyl$_{(C\leq6)}$, or substituted alkyl$_{(C\leq6)}$;
L is a group of the formula:

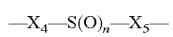

wherein:
n is 0, 1, or 2; and
$X_4$ and $X_5$ are each independently alkanediyl$_{(C\leq8)}$ or substituted alkanediyl$_{(C\leq8)}$; and
$Y_1$ and $Y_2$ are each independently alkyl$_{(C\leq12)}$, substituted alkyl$_{(C\leq12)}$, alkenyl$_{(C\leq12)}$, or substituted alkenyl$_{(C\leq12)}$; or $Y_1$ and $Y_2$ are taken together and are alkanediyl$_{(C\leq12)}$, alkenediyl$_{(C\leq12)}$, or a substituted version of either group;
or a pharmaceutically acceptable salt thereof.

In some embodiments, the polymers are further defined as:

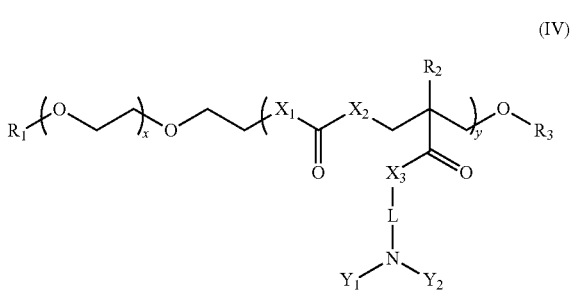
(IV)

wherein:
$R_1$ is hydrogen, alkyl$_{(C\leq8)}$, substituted alkyl$_{(C\leq8)}$, or a thiol reactive group;
x is an integer from 10 to 200;
y is an integer from 20 to 200; $X_1$ and $X_2$ are each O or NR$_a$, wherein:
$R_a$ is hydrogen, alkyl$_{(C\leq6)}$, or substituted alkyl$_{(C\leq6)}$;
$R_2$ is hydrogen, alkyl$_{(C\leq8)}$, or substituted alkyl$_{(C\leq8)}$;
$R_3$ is hydrogen, alkyl$_{(C\leq8)}$, or substituted alkyl$_{(C\leq8)}$;
$X_3$ is O or NR$_b$, wherein:
$R_b$ is hydrogen, alkyl$_{(C\leq6)}$, or substituted alkyl$_{(C\leq6)}$;
L is a group of the formula:

wherein:
n is 0, 1, or 2; and
$X_4$ and $X_5$ are each independently alkanediyl$_{(C\leq8)}$ or substituted alkanediyl$_{(C\leq8)}$; and
$Y_1$ and $Y_2$ are each independently alkyl$_{(C\leq12)}$, substituted alkyl$_{(C\leq12)}$, alkenyl$_{(C\leq12)}$, or substituted alkenyl$_{(C\leq12)}$; or $Y_1$ and $Y_2$ are taken together and are alkanediyl$_{(C\leq12)}$, alkenediyl$_{(C\leq12)}$, or a substituted version of either group;
or a pharmaceutically acceptable salt thereof.

In some embodiments, the polymers are further defined as:

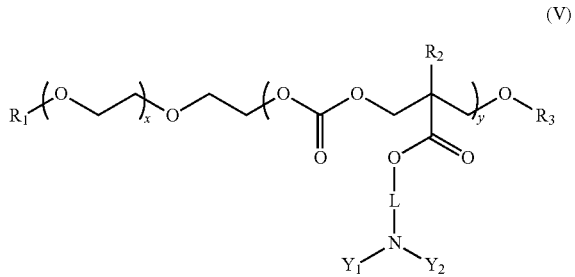

(V)

wherein:
R$_1$ is hydrogen, alkyl$_{(C\leq8)}$, substituted alkyl$_{(C\leq8)}$, or a thiol reactive group;
x is an integer from 10 to 200;
y is an integer from 20 to 200;
R$_2$ is hydrogen, alkyl$_{(C\leq8)}$, or substituted alkyl$_{(C\leq8)}$;
R$_3$ is hydrogen, alkyl$_{(C\leq8)}$, or substituted alkyl$_{(C\leq8)}$;
L is a group of the formula:

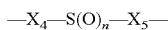

wherein:
n is 0, 1, or 2; and
X$_4$ and X$_5$ are each independently alkanediyl$_{(C\leq8)}$ or substituted alkanediyl$_{(C\leq8)}$; and
Y$_1$ and Y$_2$ are each independently alkyl$_{(C\leq12)}$, substituted alkyl$_{(C\leq12)}$, alkenyl$_{(C\leq12)}$, or substituted alkenyl$_{(C\leq12)}$; or Y$_1$ and Y$_2$ are taken together and are alkanediyl$_{(C\leq12)}$, alkenediyl$_{(C\leq12)}$, or a substituted version of either group;
or a pharmaceutically acceptable salt thereof.

In some embodiments, the polymers are further defined as:

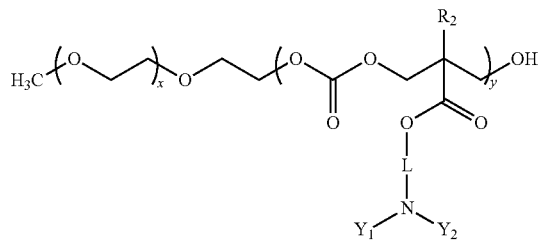

(VI)

wherein:
x is an integer from 10 to 200;
y is an integer from 20 to 200;
R$_2$ is hydrogen, alkyl$_{(C\leq8)}$, or substituted alkyl$_{(C\leq8)}$;
L is a group of the formula:

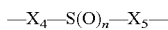

wherein:
n is 0, 1, or 2; and
X$_4$ and X$_5$ are each independently alkanediyl$_{(C\leq8)}$ or substituted alkanediyl$_{(C\leq8)}$; and
Y$_1$ and Y$_2$ are each independently alkyl$_{(C\leq12)}$, substituted alkyl$_{(C\leq12)}$, alkenyl$_{(C\leq12)}$, or substituted alkenyl$_{(C\leq12)}$;

or Y$_1$ and Y$_2$ are taken together and are alkanediyl$_{(C\leq12)}$, alkenediyl$_{(C\leq12)}$, or a substituted version of either group;
or a pharmaceutically acceptable salt thereof.

In some embodiments, p is 1. In some embodiments, q is 1. In some embodiments, m is 1, 2, or 3 such as 2. In some embodiments, X$_1$ is O. In some embodiments, X$_2$ is O. In some embodiments, X$_3$ is O.

In some embodiments, R$_1$ is alkyl$_{(C\leq8)}$ or substituted alkyl$_{(C\leq8)}$. In some embodiments, R$_1$ is alkyl$_{(C\leq8)}$ such as methyl. In some embodiments, R$_3$ is hydrogen. In some embodiments, R$_2$ is alkyl$_{(C\leq8)}$ or substituted alkyl$_{(C\leq8)}$. In some embodiments, R$_2$ is alkyl$_{(C\leq8)}$ such as methyl.

In some embodiments, X$_4$ of L is alkanediyl$_{(C\leq6)}$ or substituted alkanediyl$_{(C\leq6)}$. In some embodiments, X$_4$ of L is alkanediyl$_{(C\leq6)}$ such as —CH$_2$CH$_2$—. In some embodiments, X$_5$ of L is alkanediyl$_{(C\leq6)}$ or substituted alkanediyl$_{(C\leq6)}$. In some embodiments, X$_5$ of L is alkanediyl$_{(C\leq6)}$ such as —CH$_2$CH$_2$—. In some embodiments, n is 0.

In some embodiments, Y$_1$ is alkyl$_{(C\leq12)}$ or substituted alkyl$_{(C\leq12)}$. In some embodiments, Y$_1$ is alkyl$_{(C2-12)}$ or substituted alkyl$_{(C2-12)}$. In some embodiments, Y$_1$ is alkyl$_{(C2-12)}$. In some embodiments, Y$_1$ is methyl, ethyl, n-propyl, or n-butyl. In some embodiments, Y$_2$ is alkyl$_{(C\leq12)}$ or substituted alkyl$_{(C\leq12)}$. In some embodiments, Y$_2$ is alkyl$_{(C2-12)}$ or substituted alkyl$_{(C2-12)}$. In some embodiments, Y$_2$ is alkyl$_{(C2-12)}$. In some embodiments, Y$_2$ is methyl, ethyl, n-propyl, or n-butyl. In some embodiments, Y$_1$ and Y$_2$ are taken together and are alkanediyl$_{(C\leq12)}$ or substituted alkanediyl$_{(C\leq12)}$. In some embodiments, Y$_1$ and Y$_2$ are taken together and are alkanediyl$_{(C\leq8)}$ or substituted alkanediyl$_{(C\leq8)}$. In some embodiments, Y$_1$ and Y$_2$ are taken together and are alkanediyl$_{(C\leq8)}$ such as when Y$_1$ and Y$_2$ are taken together and are —CH$_2$CH$_2$CH$_2$CH$_2$—, —CH$_2$CH$_2$CH$_2$CH$_2$CH$_2$—, or —CH$_2$CH$_2$CH$_2$CH$_2$CH$_2$CH$_2$—.

In some embodiments, the polymers are further defined as:

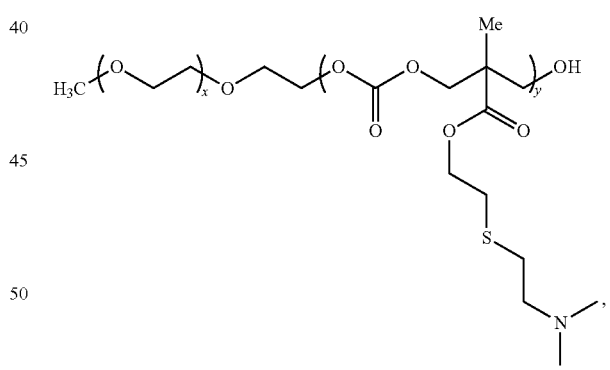

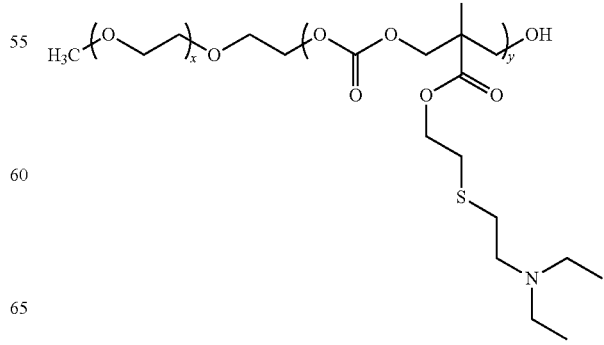

or a pharmaceutically acceptable salt thereof.

In some embodiments, x is an integer from 40 to 160 such as an integer from 80 to 150. In some embodiments, y is an integer from 40 to 180 such as an integer from 80 to 150.

In yet another aspect, the present disclosure provides micelles comprising a plurality of polymers described herein.

In still yet another aspect, the present disclosure provides compositions comprising:
(A) a polymer described herein; and
(B) a therapeutic agent;
wherein the polymer encapsulates the therapeutic agent.

In some embodiments, the polymer forms a micelle. In some embodiments, the micelle completely encapsulates the therapeutic agent. In some embodiments, the therapeutic agent is an agent which effects the immune system such as a cytokine or an immune system modulator. In some embodiments, the cytokine is IL-10, IL-2, IL-12, or IL-15. In other embodiments, the immune system modulator is cGAMP or a type 1 interferon. In other embodiments, the therapeutic agent is an antigen such as an anti-cancer antigen. In some embodiments, the anti-cancer antigen is E7 peptide.

In some embodiments, the composition is formulated as a pharmaceutical composition and further comprises an excipient. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion. In some embodiments, the pharmaceutical composition is formulated for administration via injection such as formulated for intraarterial administration, intramuscular administration, intraperitoneal administration, intratumoral administration, or intravenous administration. In some embodiments, the excipient is a vehicle such as an aqueous solution suitable for injection.

In another aspect, the present disclosure provides methods of treating a disease or disorder comprising administering to the patient in need thereof a therapeutically effective amount of a composition described herein, wherein the therapeutic agent is sufficient to treat the disease or disorder. In some embodiments, the disease or disorder is cancer. In some embodiments, the therapeutic agent is capable of modulating the immune system to target cancer. In some embodiments, the therapeutic agent generates an immune response to one or more cancer cells.

As used herein, "pH-responsive micelle," "pH-sensitive micelle," "pH-activatable micelle" and "pH-activatable micellar (pHAM) nanoparticle" are used interchangeably herein to indicate a micelle comprising one or more block copolymers, which disassociates depending on the pH (e.g., above or below a certain pH). As a non-limiting example, at a certain pH, the block copolymer is substantially in micellar form. As the pH changes (e.g., decreases), the micelles begin to disassociate, and as the pH further changes (e.g., further decreases), the block copolymer is present substantially in disassociated (non-micellar) form.

As used herein, "pH transition range" indicates the pH range over which the micelles disassociate.

As used herein, "pH transition value" ($pH_t$) indicates the pH at which half of the micelles are disassociated.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) pH changes as a function of protonation degrees of PEO-b-P(MAC-SR) copolymers with different tertiary amine substituents. Data of $PEO_{123}$-b-$P(MAC-SDMA)_{135}$ is presented separately in FIG. 4. (FIG. 1B) $pK_a$ values are inversely correlated with the log P of the repeating unit of the P(MAC-SR) segment (neutral/deprotonated state). Blue and pink points represent copolymers with linear and cyclic dialkyl tertiary amines as side groups, respectively. (FIG. 1C) pH transition sharpness ($\Delta pH_{10\%-90\%}$) as a function of log P of PEO-b-P(MAC-SR) block copolymers. Commonly used polybases (poly(ethyleneimine), chitosan, polyhistidine, polylysine) are shown for comparison (Li et al., 2016).

(FIG. 2A) Number-weighted hydrodynamic diameters and light scattering count rates as a function of protonation degree during the pH titration of $PEG_{123}$-b-$P(MAC-SC7A)_{135}$ copolymer. (FIG. 2B) TEM images and number-weighted hydrodynamic diameter distributions of $PEG_{123}$-b-$P(MAC-SC7A)_{135}$ at the protonation degrees of 95% and 85%, above and below the critical micellization protonation degree.

(FIG. 3A) Chemical structures of the copolymer and its degradation products. $^1$H NMR spectra of $PEG_{123}$-b-$P(MAC-SC7A)_{135}$ copolymer in (FIG. 3B) pH 6.5 and (FIG. 3C) pH 7.4 deuterated buffer solutions over time. Only selected regions of the spectra were presented for clarity. The complete spectra are shown in FIGS. 6 & 7. (FIG. 3D) Integration ratios of peaks (d1+d2), and peaks (d3+d4), relative to normalized proton signal of the PEO segment in pH 6.5 deuterated buffer solution. (FIG. 3E) Integration ratios of peaks (d3+d4) relative to normalized proton signal of the PEO segment in pH 6.5 and 7.4 deuterated buffer solutions.

(FIG. 5B) TEM images and number-weighted hydrodynamic diameter distributions of $PEO_{123}$-b-$P(MAC-SDMA)_{135}$ at the protonation degrees of 55% and 45%, above and below the CMPD (~50%). Scale bar: 50 nm.

FIGS. 12A-12C shows STING binding and activation of dUPS polymers. FIG. 12A Isothermal titration calorimetry (ITC) shows the PSC7A copolymer has a much higher binding affinity to STING than PSDEA. $K_d$: apparent dissociation constant. FIG. 12B Summary of $K_b$ values (binding affinity, the reciprocal of $K_d$) of different dUPS polymers to STING from ITC experiments. FIG. 12C Interferon (IFN) induction levels of THP1-ISG cells incubated with dUPS copolymers (0.5 µM for 48 h), correlating with STING binding affinity. Statistical significance was calculated by t-test: *$P<0.001$, $P<0.01$, *$P<0.05$.

FIGS. 15A-15C show short-term safety evaluation of degradable PSC7A NP and non-degradable PC7A NP. FIG. 15A C57BL/6 mice (n=4 per group) were subcutaneously injected with PBS, 300 µg PSC7A NP, or 300 µg PC7A NP on the right flank. FIG. 15B Serum concentrations of Alanine Aminotransferase (ALT), Aspartate Aminotransferase (AST), Urea and Creatinine levels were quantitatively measured by Abcam™ Assay Kit 24 hours after injection. FIG. 15C Serum concentrations of Interleukin-6 (IL-6), Interleukin-10 (IL-10), Monocyte Chemoattractant Protein-1 (MCP-1), Interferon-γ (IFN-γ), Tumor Necrosis Factor (TNF), and Interleukin-12p70 (IL-12p70) protein levels were quantitatively measured by BD™ CBA Mouse Inflammation Kit 24 hours after injection. Statistical significance was calculated by t-test: *$P<0.001$, $P<0.01$, *$P<0.05$.

FIG. 17A C57BL/6 mice were subcutaneously injected with PBS, 300 µg PSC7A NP, or 300 µg PC7A NP on the right flank. Inflammatory nodules formed at the injection sites in PSC7A NP and PC7A NP groups. The surface areas of the nodules were calculated based on an ellipse model. FIG. 17B Change of nodule surface areas over time. FIG. 17C Left: photographs of skin tissues taken from the injection sites on day 60, from top to bottom are mice treated with PC7A NP, PSC7A NP and PBS. Right: magnification of skin tissues from PSC7A and PC7A groups. FIG. 17C Left: H&E staining of formalin-fixed, paraffin-embedded skin tissues (injection sites) on day 60, from top to bottom are mice treated with PC7A NP, PSC7A NP and PBS. Scale bar: 2.5 mm. Middle: magnification of a nodule surrounded by granulomatous inflammation from PC7A group. Scale bar: 250 µm. Inset: magnification of the area marked by a square. The bottom left, top left and right arrows represent the macrophage, lymphocyte and neutrophil, respectively. Scale bar: 50 µm. Right: magnification of skin tissue from PSC7A group. Scale bar: 250 µm.

DESCRIPTION OF ILLUSTRATIVE EMBODIMENTS

Figures 1A, 1B, 1C:
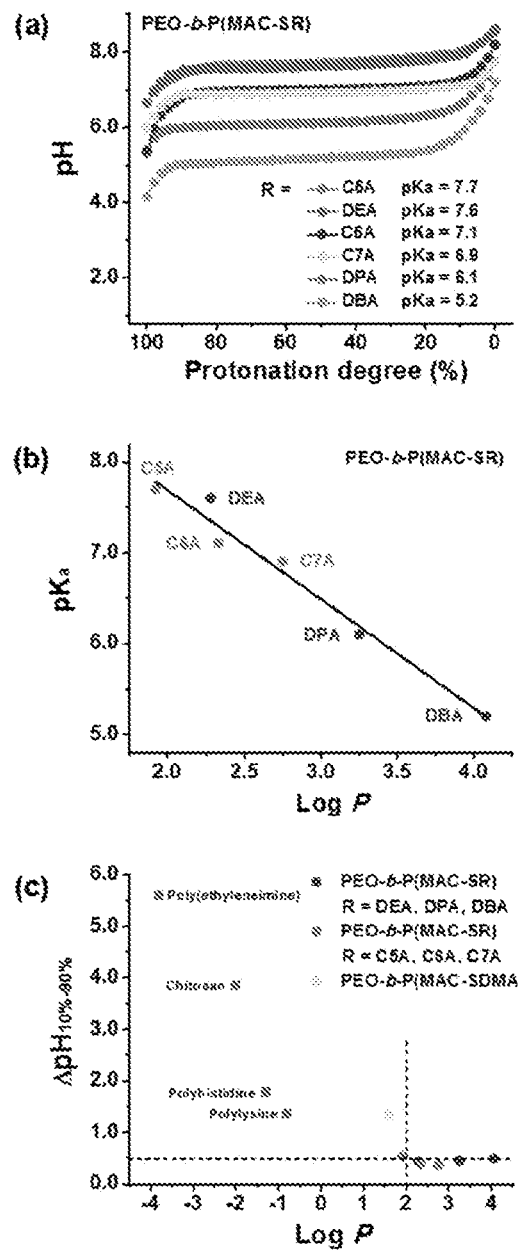
FIGS. 1A-1C show the characterization of ultra-pH sensitive response of biodegradable UPS copolymers.

In some aspects, the present disclosure provides a polymer which can form a pH responsive nanoparticle which dissembles above a particular transition pH and contains a degradable backbone. In some embodiments, these polymers possess a sharp pH transition value and are contain one or more degradable groups which speeds up clearance of the polymer. These polymers may possess a wide range of pH transition points allows for a wide range of application such as delivering drug compounds to specific tissues. In some aspects, the present disclosure provides methods of using these polymers in a pH responsive system as described above such as delivery therapeutic agents to the body including such therapeutic agents such as immune system modulators which may be used to treat cancer.

A. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo"

means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof, "mercapto" means —SH; and "thio" means =S; "thiocarbonyl" means —C(=S)—; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example,

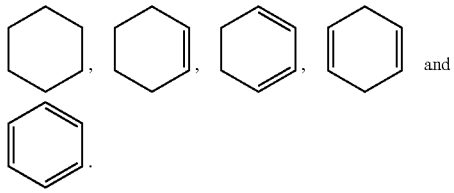

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⌇", when drawn perpendicularly across a bond (e.g.

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⫼" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

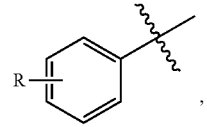

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

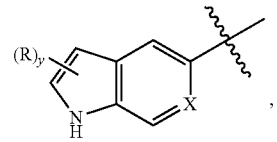

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. Except as noted below, every carbon atom is counted to determine whether the group or compound falls with the specified number of carbon atoms. For example, the group dihexylamino is an example of a dialkylamino$_{(C=12)}$ group; however, it is not an example of a dialkylamino$_{(C=6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$.

The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "thiol reactive group" is a functional group which is capable of undergoing a reaction with mercapto group (—SH) to form a covalent bond. Such groups are well known in the literature. Two prototypical groups include haloacetamides such as iodoacetamides as well as maleimides. These groups may be used to react with the mercapto group of a cysteine residue to form a covalent bond to the sulfur atom.

B. BLOCK COPOLYMERS

The pH-responsive micelles and nanoparticles disclosed herein comprise block copolymers. A block copolymer comprises a hydrophilic polymer segment and a hydrophobic polymer segment. The hydrophobic polymer segment is pH sensitive. For example, the hydrophobic polymer segment may comprise an ionizable amine group to render pH sensitivity. The block copolymers form pH-activatable micellar (pHAM) nanoparticles based on the supramolecular self-assembly of these ionizable block copolymers. At higher pH, the block copolymers assemble into micelles, whereas at lower pH, ionization of the amine group in the hydrophobic polymer segment results in dissociation of the micelle. The ionizable groups may act as tunable hydrophilic/hydrophobic blocks at different pH values, which may directly affect the dynamic self-assembly of micelles.

In some embodiments, the present polymers contain one or more blocks which is constructed using a degradable polymer base such as a polycarbonate or a polyurea. These components may be used to construct the hydrophobic polymer segment. In some embodiments, these polymer segments contain one monomer unit to form a homopolymer. In other embodiments, the polymer segments may contain two or more monomer units to form the polymer segments. If the polymer segment contains two or more monomer units, then the monomer units may be either a single block of one unit followed by a distinct block for each of the additional monomer units or the different monomer units may be randomly dispersed throughout the entire polymer block.

The polymers described herein are shown, for example, above, in the summary section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

The polymers described herein may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. The polymers may occur as racemates and racemic mixtures, single enantiomers, diastereomeric mixtures and individual diastereomers. In some embodiments, a single diastereomer is obtained. The chiral centers of the polymers can have the S or the R configuration. In some embodiments, the present polymers may contain two or more atoms which have a defined stereochemical orientation.

Chemical formulas used to represent polymers described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the polymers described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, polymers described herein exist in salt or non-salt form. With regard to the salt form(s), in some embodiments the particular anion or cation forming a part of any salt form of a polymer provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

C. MICELLE SYSTEMS AND COMPOSITIONS

The systems and compositions disclosed herein utilize either a single micelle or a series of micelles tuned to different pH levels. Furthermore, the micelles have a narrow pH transition range. In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.25, less than about 0.2, or less than about 0.1 pH unit.

The narrow pH transition range advantageously provides a sharper pH response that can result in complete turn-on of the fluorophores with subtle changes of pH.

The size of the micelles will typically be in the nanometer scale (i.e., between about 1 nm and 1 μm in diameter). In some embodiments, the micelle has a size of about 10 to about 200 nm. In some embodiments, the micelle has a size of about 20 to about 100 nm. In some embodiments, the micelle has a size of about 30 to about 50 nm.

D. TARGETING MOIETIES

The micelles and nanoparticles may further comprise a targeting moiety. The targeting moiety may be used to target the nanoparticle or micelle to, for example, a particular cell surface receptor, cell surface marker, or to an organelle (e.g., nucleus, mitochondria, endoplasmic reticulum, chloroplast, apoplast, or peroxisome). Such targeting moieties will be advantageous in the study of receptor recycling, marker recycling, intracellular pH regulation, endocytic trafficking.

The targeting moiety may be, for example, an antibody or antibody fragment (e.g., Fab' fragment), a protein, a peptide (e.g., a signal peptide), an aptamer, or a small molecule (e.g., folic acid). The targeting moiety may be conjugated to the block copolymer (e.g., conjugated to the hydrophilic polymer segment) by methods known in the art. The selection of targeting moiety will depend on the particular target. For example, antibodies, antibody fragments, small molecules, or binding partners may be more appropriate for targeting cell surface receptors and cell surface markers, whereas peptides, particularly signal peptides, may be more appropriate for targeting organelles.

E. ANTIGENS

In some aspects, the present disclosure provides compositions one or more antigenic components. An antigen is a substance which promotes an immune response such that antibodies are generated against the substance specifically. Some substances are more immunogenic and thus the immune system will readily develop an appropriate immune response but other substances require assistance to generate an immune response sufficient to generate antibodies against the antigen. Most cancers may require additional activation to enhance the generation of antibodies against the antigen. Some non-limiting examples of antigens include proteins or fragments thereof of cancer specific surface proteins or surface proteins overexpressed by cancer cells.

i. Cancer

A variety of different peptides, protein fragments, or proteins may be used as antigens in the present compositions. Some non-limiting examples include 5T4, 707-AP (707 alanine proline), 9D7, AFP (α-fetoprotein), AlbZIP HPG1, α5β1-Integrin, α5β6-Integrin, α-methylacyl-coenzyme A racemase, ART-4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD 19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT-9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumour cell-associated extracellular matrix metalloproteinase inducer), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CAIX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumour-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor α 2 chain), IL-2R, IL-5, immature laminin receptor, kallikrein 2, kallikrein 4, Ki67, KIAA0205, KK-LC-1 (Kita-kyushu lung cancer antigen 1), KM-HN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigen-A4), MAGE-A6 (melanoma antigen-A6), MAGE-A9 (melanoma-antigen-A9), MAGE-B1 (melanoma-antigen-B 1), MAGE-B 10 (melanoma-antigen-B 10), MAGE-B16 (melanoma-antigen-B16), MAGE-B17 (melanoma-antigen-B17), MAGE-B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucosaminyltransferase-V, Neo-PAP (Neo-poly(A) polymerase), NGEP, NMP22, NPM/ALK (nucleophosmin/anaplastic lymphoma kinase fusion protein), NSE (neuronspecific enolase), NY-ESO-1 (New York esophagus 1), NY-ESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGE-like protein-4), PAI-1 (plasminogen activator inhibitor 1), PAI-2 (plasminogen activator inhibitor 2), PAP (prostate acid phosphatase), PART-1, PATE, PDEF, Pim-1-Kinase, Pin1 (Propyl isomerase), POTE, PRAME (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumour 1), SART-2 (squamous antigen rejecting tumour 1), SART-3 (squamous antigen rejecting tumour 1), SCC (squamous cell carcinoma antigen), Sp17 (sperm protein 17), SSX-1 (synovial sarcoma X breakpoint 1), SSX-2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP-2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumour gene), or may comprise e.g. mutant antigens expressed in cancer diseases selected from the group comprising, without being limited thereto, α-actinin-4/m, ARTC1/m, bcr/abl (breakpoint cluster region-Abelson fusion protein), O-Catenin/m (0-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R170I (arginine to isoleucine exchange at residue 170 of the α-helix of the α2-domain in the HLA-A2 gene), HLA-A11/m, HLA-A2/m, HSP70-2M (heat shock protein 70-2 mutated), KIAA0205/m, K-Ras/m, LDLR-FUT (LDR-Fucosyltransferase fusion protein), MART2/m, ME1/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS-9/m, p53/m, Pm1/RARα (promyelocytic leukemia/retinoic acid receptor α), PRDX5/m, PTPRK/m (receptor-type proteintyrosine phosphatase κ), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFβRII (TGFβ receptor II), TPI/m (triosephosphate isomerase).

F. KITS

The present disclosure also provides kits. Any of the components disclosed herein may be combined in a kit. In certain embodiments the kits comprise a pH-responsive system or composition as described above.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed.

However, various combinations of components may be comprised in a container. In some embodiments, all of the micelle populations in a series are combined in a single container. In other embodiments, some or all of the micelle population in a series are provided in separate containers.

The kits of the present disclosure also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

G. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Synthetic Characterizations, Materials, and Methods

1. Materials

All reagents were purchased from commercial sources or synthesized and used without further purification unless specified. They were poly(ethylene glycol) methyl ether (mPEG$_{5k}$-OH, M$_n$=5.4×10$^3$ g/mol measured by $^1$H NMR), 1-(3,5-bis-trifluoromethyl-phenyl)-3-cyclohexylthiourea (TU, synthesized) (Natarajan et al., 2005), 1,8-diazabicyclo [5.4.0]undec-7-ene (DBU, ≥99%, Sigma-Aldrich), dipropylamine (DPA, 99%, Sigma-Aldrich), dibutylamine (DBA, ≥99.5%, Sigma-Aldrich), pyrrolidine (C5A, ≥99%, Sigma-Aldrich), piperidine (C6A, ≥99.5%), hexamethyleneimine (C7A, 99%, Sigma-Aldrich), ethylene sulfide (98%, Sigma-Aldrich), 2,2-dimethoxy-2-phenylacetophenone (DMPA, 99%, Sigma-Aldrich). 2-Dimethylaminoethanethiol hydrochloride (DMA-SH·HCl, 95%) and 2-diethylaminoethanethiol hydrochloride (DEA-SH·HCl, 95%) were purchased from Sigma-Aldrich. Other aminothiol hydrochloride molecules (shown below) were synthesized as reported (Hao et al., 2015).

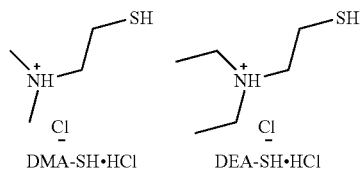

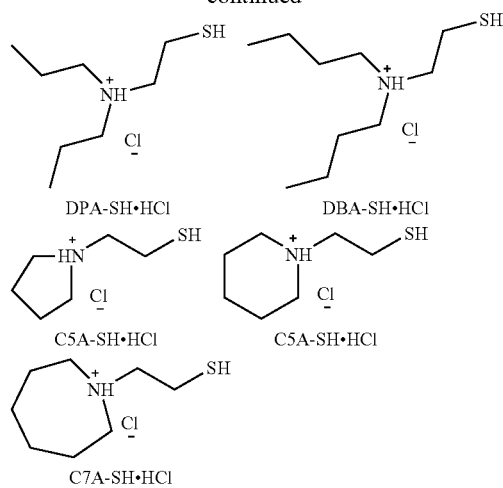

Synthesis of PEO-b-PMAC Copolymer

First, 5-methyl-5-allyloxycarbonyl-1,3-dioxan-2-one (MAC) monomer was synthesized as reported (Hu et al., 2007). PEO-b-PMAC copolymer was synthesized by ring opening polymerization (ROP) with mPEG$_{5k}$-OH as the initiator ([monomer]/[initiator]=200). Typically, a Schlenk reaction flask was charged with 0.4 g mPEG$_{5k}$-OH, 3.2 g MAC monomer and 16.0 mL dichloromethane (DCM) in a glove box filled with purified argon. After three freeze-pump-thaw cycles, 0.6 g TU and 0.16 mL DBU were introduced to start the polymerization. The reaction was placed in an oil bath at 30° C. for 15 h, then quenched by the addition of benzoic acid. The DCM solvent was removed by evaporation, and the concentrated residue was precipitated into an excess amount of cold ether. The purification process was repeated twice to remove any unreacted starting materials and impurity. The resulting PEO-b-PMAC copolymers were characterized by 400 MHz $^1$H NMR, gel permeation chromatography (GPC, Viscotech GPCmax, PLgel 5 μm MIXED-D columns by Polymer Labs. THF with 1% v/v TEA was used as eluent at 1.0 mL/min). For PEG$_{123}$-b-PMAC$_{125}$, $^1$H NMR (400 MHz, CDCl$_3$, 25° C.): δ 5.92-5.84 (m, 1H, —CH=CH$_2$), 5.33-5.23 (m, 2H, —CH=CH$_2$), 4.63 (br, 2H, —OCH$_2$CH=CH$_2$), 4.38-4.22 (m, 4H, —OCH$_2$—C—CH$_2$O—), 3.64 (s, 2H, —OCH$_2$CH$_2$), 3.38 (s, 3H, —OCH$_3$), 1.28 (s, 3H, CH$_3$), 1.22 (s, 3H, C(CH$_3$) CH$_2$OH). GPC (THF, IR): M$_n$=2.58×10$^4$ g/mol, M$_w$=3.47× 10$^4$ g/mol, M$_w$/M$_n$=1.35).

Syntheses of PEO-b-P(MAC-SR·HCl) Copolymers

PEO-b-P(MAC-SR·HCl) copolymer was synthesized by the thiol-ene reaction between allyl-containing PEO-b-PMAC and the aminothiol hydrochloride. Below we chose the synthesis of PEO-b-P(MAC-SDEA·HCl) as an example. First, 0.1 g PEO$_{123}$-b-PMAC$_{125}$ (0.419 mmol) was dissolved in 15 mL DMF in a quartz flask and stirred under nitrogen for 10-20 mins. Then 1.06 g DEA-SH·HCl (6.29 mmol) and 21.5 mg DMPA (0.084 mmol) were added into the flask. After nitrogen purge for additional 20 mins, the flask was put under a UV light (365 nm) to initiate the reaction. After 12 h, the reaction mixture was dialyzed in distilled water and lyophilized to obtain a white powder. The series of PEO-b-P(MAC-SR·HCl) copolymers were verified by $^1$H NMR and GPC. The results are summarized in Table 1.

TABLE 1

Characterization of PEO-b-P(MAC-SR·HCl) copolymers.

| Copolymer | $M_{n,\ HNMR}$ (g·mol$^{-1}$) | Number of repeating units of P(MAC-SR·HCl) | $M_{w,\ GPC}$ (g·mol$^{-1}$)[c] | $M_{n,\ GPC}$ (g·mol$^{-1}$)[c] | PDI[c] |
|---|---|---|---|---|---|
| PEO$_{123}$-b-P(MAC-SDMA·HCl)$_{135}$ | $5.2 \times 10^4$ | 135[a] | $3.8 \times 10^4$ | $2.4 \times 10^4$ | 1.58 |
| PEO$_{123}$-b-P(MAC-SDEA·HCl)$_{115}$ | $4.8 \times 10^4$ | 115[b] | $3.2 \times 10^4$ | $2.0 \times 10^4$ | 1.56 |
| PEO$_{123}$-b-P(MAC-SDPA·HCl)$_{115}$ | $5.1 \times 10^4$ | 115[b] | $3.7 \times 10^4$ | $2.4 \times 10^4$ | 1.52 |
| PEO$_{123}$-b-P(MAC-SDBA·HCl)$_{105}$ | $5.5 \times 10^4$ | 105[b] | $3.3 \times 10^4$ | $2.0 \times 10^4$ | 1.65 |
| PEO$_{123}$-b-P(MAC-SC5A·HCl)$_{110}$ | $4.6 \times 10^4$ | 110[b] | $3.0 \times 10^4$ | $1.9 \times 10^4$ | 1.58 |
| PEO$_{123}$-b-P(MAC-SC6A·HCl)$_{115}$ | $5.5 \times 10^4$ | 115[b] | $3.2 \times 10^4$ | $2.2 \times 10^4$ | 1.49 |
| PEO$_{123}$-b-P(MAC-SC7A·HCl)$_{135}$ | $5.9 \times 10^4$ | 135[a] | $3.9 \times 10^4$ | $2.7 \times 10^4$ | 1.45 |

[a]The number of repeating units for the PEO-b-PMAC copolymer precursor is 140.
[b]The number of repeating units for the PEO-b-PMAC copolymer precursor is 125.
[c]$M_{w,\ GPC}$, $M_{n,\ GPC}$ and PDI ($M_{w,\ GPC}/M_{n,\ GPC}$) were obtained by using polystyrene as standard and THF (1% v/v TEA) as eluting solvent in GPC.

PEO$_{123}$-b-P(MAC-SDMA·HCl)$_{135}$ (PSDMA) $^1$H NMR (400 MHz, CDCl$_3$, 25° C.): δ 4.29 (s, 4H, —OCH$_2$—C—CH$_2$O—), 4.25 (t, 2H, —OCH$_2$CH$_2$—), 3.64 (s, 2H, —OCH$_2$CH$_2$), 3.38 (s, 3H, —OCH$_3$), 3.35-3.31 (t, 2H, —SCH$_2$CH$_2$N—), 3.02-2.98 (m, 2H, —SCH$_2$CH$_2$N—), 2.92 (s, 6H, —N(CH$_3$)$_2$), 2.66 (t, 2H, —OCH$_2$CH$_2$CH$_2$S—), 2.00-1.95 (m, 2H, —OCH$_2$CH$_2$CH$_2$S—), 1.28 (s, 3H, —CH$_3$).

PEO$_{123}$-b-P(MAC-SDEA·HCl)$_{115}$ (PSDEA) $^1$H NMR (400 MHz, CDCl$_3$, 25° C.): δ 4.29 (s, 4H, —OCH$_2$—C—CH$_2$O—), 4.25 (t, 2H, —OCH$_2$CH$_2$—), 3.64 (s, 2H, —OCH$_2$CH$_2$), 3.38 (s, 3H, —OCH$_3$), 3.20-3.14 (m, 6H, —SCH$_2$CH$_2$N(CH$_2$CH$_3$)$_2$—), 3.03-3.00 (m, 2H, —SCH$_2$CH$_2$N—), 2.66 (t, 2H, —OCH$_2$CH$_2$CH$_2$S—), 2.00-1.95 (m, 2H, —OCH$_2$CH$_2$CH$_2$S—), 1.38 (t, 6H, —N(CH$_2$CH$_3$)$_2$), 1.28 (s, 3H, —CH$_3$).

PEO$_{123}$-b-P(MAC-SDPA·HCl)$_{115}$ (PSDPA) $^1$H NMR (400 MHz, CDCl$_3$, 25° C.): δ 4.29 (s, 4H, —OCH$_2$—C—CH$_2$O—), 4.25 (t, 2H, —OCH$_2$CH$_2$—), 3.64 (s, 2H, —OCH$_2$CH$_2$), 3.38 (s, 3H, —OCH$_3$), 3.19 (s, 2H, —SCH$_2$CH$_2$N—), 3.04-2.98 (m, 2H, —SCH$_2$CH$_2$N— and —N(CH$_2$CH$_2$CH$_3$)$_2$), 2.66 (t, 2H, —OCH$_2$CH$_2$CH$_2$S—), 2.00-1.95 (m, 2H, —OCH$_2$CH$_2$CH$_2$S—), 1.85-1.81 (m, 4H, —N(CH$_2$CH$_2$CH$_3$)$_2$), 1.28 (s, 3H, —CH$_3$), 1.01 (t, 6H, —N(CH$_2$CH$_2$CH$_3$)$_2$).

PEO$_{123}$-b-P(MAC-SDBA·HCl)$_{105}$ (PSDBA) $^1$H NMR (400 MHz, CDCl$_3$, 25° C.): δ 5.92-5.84 (m, 1H, —CH=CH$_2$), 5.33-5.23 (m, 2H, —CH=CH$_2$), 4.64-4.63 (d, 2H, —OCH$_2$CH=CH$_2$), 4.34-4.28 (m, 4H, —OCH$_2$—C—CH$_2$O—), 4.24 (t, 2H, —OCH$_2$CH$_2$—), 3.64 (s, 2H, —OCH$_2$CH$_2$), 3.38 (s, 3H, —OCH$_3$), 2.92 (m, 2H, —SCH$_2$CH$_2$N—), 2.82 (m, 2H, —SCH$_2$CH$_2$N—), 2.75 (m, 4H, —N(CH$_2$CH$_2$CH$_2$CH$_3$)$_2$), 2.62 (t, 2H, —OCH$_2$CH$_2$CH$_2$S—), 1.98-1.93 (m, 2H, —OCH$_2$CH$_2$CH$_2$S—), 1.60 (s, 4H, —N(CH$_2$CH$_2$CH$_2$CH$_3$)$_2$), 1.39-1.33 (m, 4H, —N(CH$_2$CH$_2$CH$_2$CH$_3$)$_2$), 1.29-1.29 (m, 6H, —CH$_3$), 0.95 (t, 6H, —N(CH$_2$CH$_2$CH$_2$CH$_3$)$_2$). A small percentage of allyl group on PMAC did not fully react with DBA-SH·HCl due to the steric hindrance of the dibutyl groups.

PEO$_{123}$-b-P(MAC-SC5A·HCl)$_{110}$ (PSC5A) $^1$H NMR (400 MHz, CDCl$_3$, 25° C.): δ 4.29 (s, 4H, —OCH$_2$—C—CH$_2$O—), 4.25 (t, 2H, —OCH$_2$CH$_2$—), 3.64 (s, 2H, —OCH$_2$CH$_2$), 3.38 (s, 3H, —OCH$_3$), 3.55-3.29 (m, 6H, —SCH$_2$CH$_2$N(CH$_2$CH$_2$)$_2$), 3.01 (m, 2H, —SCH$_2$CH$_2$N—), 2.66 (t, 2H, —OCH$_2$CH$_2$CH$_2$S—), 2.11 (s, 4H, —N(CH$_2$CH$_2$)$_2$), 2.00-1.95 (m, 2H, —OCH$_2$CH$_2$CH$_2$S—), 1.28 (s, 3H, —CH$_3$).

PEO$_{123}$-b-P(MAC-SC6A·HCl)$_{115}$ (PSC6A) $^1$H NMR (400 MHz, CDCl$_3$, 25° C.): δ 4.29 (s, 4H, —OCH$_2$—C—CH$_2$O—), 4.25 (t, 2H, —OCH$_2$CH$_2$—), 3.64 (s, 2H, —OCH$_2$CH$_2$), 3.38 (s, 3H, —OCH$_3$), 3.21 (br, 6H, —SCH$_2$CH$_2$N(CH$_2$CH$_2$)$_2$CH$_2$), 3.07 (s, 2H, —SCH$_2$CH$_2$N—), 2.66 (t, 2H, —OCH$_2$CH$_2$CH$_2$S—), 2.00 (m, 6H, —OCH$_2$CH$_2$CH$_2$S— and —N(CH$_2$CH$_2$)$_2$CH$_2$), 1.68 (m, 2H, —N(CH$_2$CH$_2$)$_2$CH$_2$), 1.28 (s, 3H, —CH$_3$).

PEO$_{123}$-b-P(MAC-SC7A·HCl)$_{135}$ (PSC7A) $^1$H NMR (400 MHz, CDCl$_3$, 25° C.): δ 4.29 (s, 4H, —OCH$_2$—C—CH$_2$O—), 4.25 (t, 2H, —OCH$_2$CH$_2$—), 3.64 (s, 2H, —OCH$_2$CH$_2$), 3.38 (s, 3H, —OCH$_3$), 3.26 (s, 2H, —SCH$_2$CH$_2$N—), 3.23-3.21 (m, 4H, —N(CH$_2$CH$_2$CH$_2$)$_2$), 2.66 (t, 2H, —OCH$_2$CH$_2$CH$_2$S—), 2.00-1.95 (m, 6H, —OCH$_2$CH$_2$CH$_2$S— and —N(CH$_2$CH$_2$CH$_2$)$_2$), 1.74 (s, 2H, —N(CH$_2$CH$_2$CH$_2$)$_2$), 1.28 (s, 3H, —CH$_3$).

Preparation of Micellar Nanoparticles

PEO-b-P(MAC-SC7A) is used as an example. In a typical procedure, 10 mg PEO$_{123}$-b-P(MAC-SC7A·HCl)$_{135}$ copolymer was dissolved in distilled water with 150 mM NaCl. NaOH solution was added to adjust the final pH value above 8.0. The excess NaOH and salts were removed by three cycles of ultracentrifugation using 3000 Da molecular weight cutoff centrifugal tube. Distilled water was added to the micelle solution to adjust the polymer concentration to 1.0 mg/mL.

pH Titration Experiments

PEO-b-P(MAC-SC7A) is used as an example. In a typical experiment, 10 mg PEO$_{123}$-b-P(MAC-SC7A·HCl)$_{135}$ copolymer was first dissolved in 10 mL distilled water to make the polymer concentration at 1.0 mg/mL. NaCl was added to adjust the salt concentration to 150 mM. Then NaOH solution was added to completely deprotonate the PEO$_{123}$-b-P(MAC-SC7A·HCl)$_{135}$ copolymer. pH titration was carried out by adding small volumes (1 μL in increments) of 0.5 M HCl solution under stirring. The pH values were measured by a Mettler Toledo pH meter with a microelectrode. The pH decrease in the whole range was monitored as a function of total added HCl volume. The complete protonated state (100% protonation degree) and deprotonated state (0% protonation degree) were determined by the two extreme value points of the 1$^{st}$ derivation of pH titration curves. At selected protonation degree, 100 μL of polymer solution was taken out for dynamic light scattering measurements (DLS, Malvern Nano-ZS model, He—Ne laser, λ=633 nm). Other PEO-b-P(MAC-SR) copolymers followed the similar titration procedure.

TEM Images of Different Copolymers

PEO$_{123}$-b-P(MAC-SC7A·HCl)$_{135}$ was first dissolved in distilled water to make the polymer concentration at 1.0 mg/mL. NaCl was added to adjust the salt concentration to 150 mM. Corresponding volumes of 0.5 M NaOH were added to adjust the protonation degrees to 95% and 85%, based on the titration coordinate. The polymer solutions were diluted to 0.2 mg/mL and dropped on the copper grid. After the grid was dried, distilled water was used to rinse the grid for several seconds to remove the NaCl before the addition of phosphotungstic acid (PTA) for negative staining. Similarly, PEO$_{123}$-b-P(MAC-SDMA)$_{135}$ copolymer with the protonation degrees of 55% and 45% were imaged by TEM.

Degradation Studies of PEO$_{123}$-b-P(MAC-SC7A)$_{135}$ in pH 6.5 and 7.4 Buffers The deuterated phosphate buffer solutions at pH 6.5 and 7.4 were prepared by Na$_2$HPO$_4$ and NaH$_2$PO$_4$ in D$_2$O (50 mM). NaCl was added to reach a final concentration at 150 mM. In pH 6.5 solution, 5.0 mg PEO$_{123}$-b-P(MAC-SC7A·HCl)$_{135}$ copolymer was dissolved in 1.0 mL deuterated phosphate buffer solution to make the polymer concentration to 5.0 mg/mL. The pH of the polymer solution was further adjusted to 6.5 by concentrated NaOD and DCl solutions. The tube was then sealed and placed into the 37° C. shaker with a speed of 150 rpm. At certain times, the polymer solution was transferred to NMR tube for $^1$H NMR measurement. The pH of the polymer solution was adjusted every other day. The pH 7.4 solution study followed the similar procedure.

Isothermal Titration Calorimetry (ITC)

ITC was used to measure the binding affinities between STING dimer and dUPS copolymers using a Marvin ITC200 microcalorimeter. Titrations were performed at 20° C. in buffer containing 25 mM HEPES (pH 6.5). The titration traces were integrated by NITPIC, and the curves were fitted by SEDFIT. The figures were prepared using GUSSI (biophysics.swmed.edu/MBR/software.html).

STING Reporter Experiments

THP1-ISG cells (5×10$^5$ cells/mL) were incubated with phorbol 12-myristate 13-acetate (PMA) in complete medium (RPMI-1640, 10% fetal bovine serum, 100 U/mL penicillin G sodium and 100 μg/mL streptomycin) at 37° C. in 5% CO$_2$ and normal O$_2$ level for 48 h and replenished with fresh medium for another 24 h. Then the cells were incubated with fresh medium with different dUPS copolymers (0.5 μM) for 48 h. The levels of IRF-induced Lucia luciferase in the cell culture supernatant were assessed with QUANTI-Luc™, a luciferase detection reagent.

PSC7A Vaccine and Tumor Therapy Experiments

The nanovaccine was made by physically mixing tumor specific antigenic peptides and PSC7A nanoparticles. Non-degradable PC7A based nanovaccines were used for comparison. Six- to eight-week-old C57BL/6 mice were inoculated with 2×10$^5$ TC-1 cells or B16F10 melanoma cells subcutaneously on their right thighs. In TC-1 tumor model, mice were injected subcutaneously into the tail base of PBS, E7p only (0.5 μg), PSC7A NP only (30 μg), low-dose PSC7A nanovaccine (0.1 μg E7p in 6 μg PSC7A NP), high-dose PSC7A nanovaccine (0.5 μg E7p in 30 μg PSC7A NP) and high-dose PC7A nanovaccine (0.5 μg E7p in 30 μg PC7A NP) on day 8, 14, 24 after inoculation. In B16F10 tumor model, mice were injected subcutaneously into the tail base of PBS, Trp1,2 only (0.5 μg Trp1$_{214-237}$ and 0.5 μg Trp2$_{173-196}$), PSC7A NP only (30 μg), low-dose PSC7A nanovaccine (0.1 μg Trp1 and 0.1 μg Trp2 in 6 μg PSC7A NP), high-dose PSC7A nanovaccine (0.5 μg Trp1 and 0.5 μg Trp2 in 30 μg PSC7A NP) and high-dose PC7A nanovaccine (0.5 μg Trp1 and 0.5 μg Trp2 in 30 μg PC7A NP) on day 5, 10, 15 after inoculation. Tumor growth was subsequently measured using a digital caliper and calculated as 0.5× length×width$^2$. Mice were sacrificed when the tumor volumes reached 2000 mm$^3$.

Statistical Analysis

Statistical analysis was performed using Origin and Graphpad Prism. Data are expressed as means±s.e.m. Data were analyzed by t-test and considered statistically significant if P<0.05 (*P<0.001, P<0.01, *P<0.05).

Example 2: Synthesis and Characterization of a Library of pH Responsive Biodegradable Polymers Scheme 1 illustrates the synthesis of biodegradable UPS copolymers using ring-opening polymerization (ROP). (Chen et al., 1997; Brannigan and Dove, 2017; Feng et al., 2012) First, an allyl functionalized block copolymer, poly (ethylene oxide)-b-poly(5-methyl-5-allyloxycarbonyl-1,3-dioxan-2-one) (PEO-b-PMAC) was synthesized using methoxy-terminated polyethylene glycol (PEO) (mPEG$_{5k}$-OH, M$_n$=5.4×10$^3$ g/mol measured by $^1$H NMR) as a macroinitiator and 5-methyl-5-allyloxycarbonyl-1,3-dioxan-2-one (MAC) as the cyclic monomer in dichloromethane (DCM). An organic co-catalyst of 1-(3,5-bis-trifluoromethyl-phenyl)-3-cyclohexylthiourea (TU) and 1,8-diazabicyclo[5.4.0]undec-7-ene (DBU) was used. The reaction mixture was heated at 30° C. for 15 h to yield the PEO-b-PMAC copolymer with 125-140 repeating units in the PMAC segment measured by $^1$H NMR. To render pH sensitivity, PEO-b-PMAC was further reacted with a series of protonated tertiary amines (R·HCl) by thiol-ene reactions under UV light (365 nm, Scheme 1). As a result, a library of biodegradable ultra-pH sensitive copolymers PEO-b-P(MAC-SR·HCl) were synthesized in the protonated states (Table 1). PSR was used to refer to the block copolymer PEO-b-P(MAC-SR·HCl) and its deprotonated state below.

Scheme 1. Synthesis of PEO-b-P(MAC-SR·HCl) by ring-opening polymerization and thiol-ene reactions. The final copolymers consist of a hydrophilic PEO segment, a biodegradable polycarbonate backbone, and ionizable tertiary amines lending pH sensitivity.

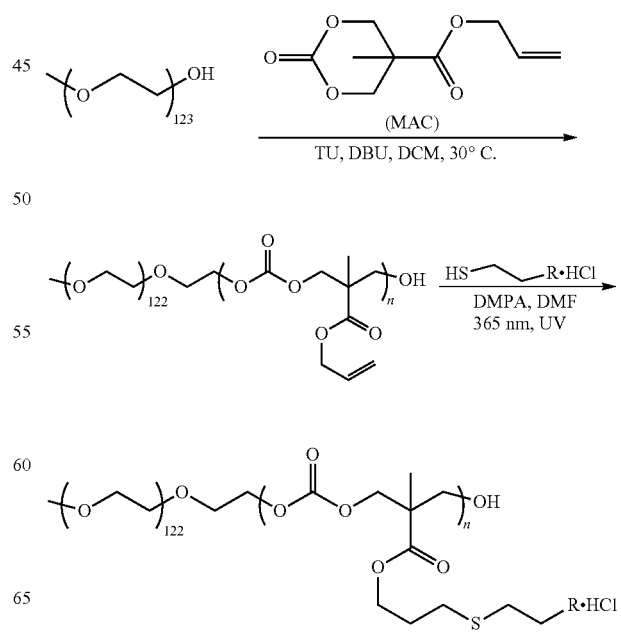

-continued

R =

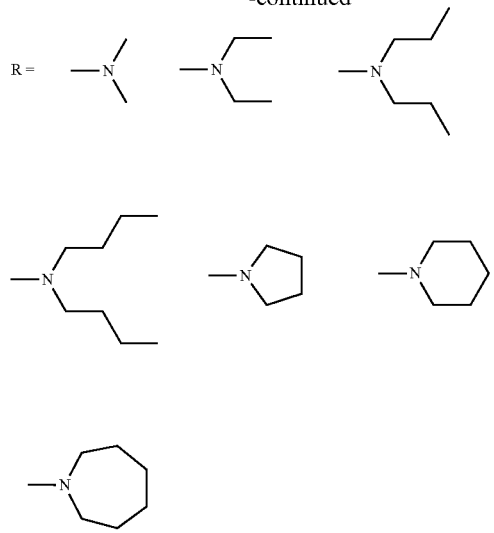

A pH titration of the newly synthesized series of dUPS copolymers (1.0 mg/mL) was carried out in the presence of 150 mM NaCl to mimic the physiological salt concentration. Data are presented as the pH over the protonation degree of the tertiary amine residues on the copolymer. The protonation degree was calculated as the molar percentage of the total amines in the protonated form. The apparent $pK_a$ of each copolymer was measured as the pH where the protonation degree is 50%. To evaluate the sharpness in pH transition, the $\Delta pH_{10\%-90\%}$, the pH range between 10% and 90% protonation degrees, was measured for each copolymer.

Figure 4:
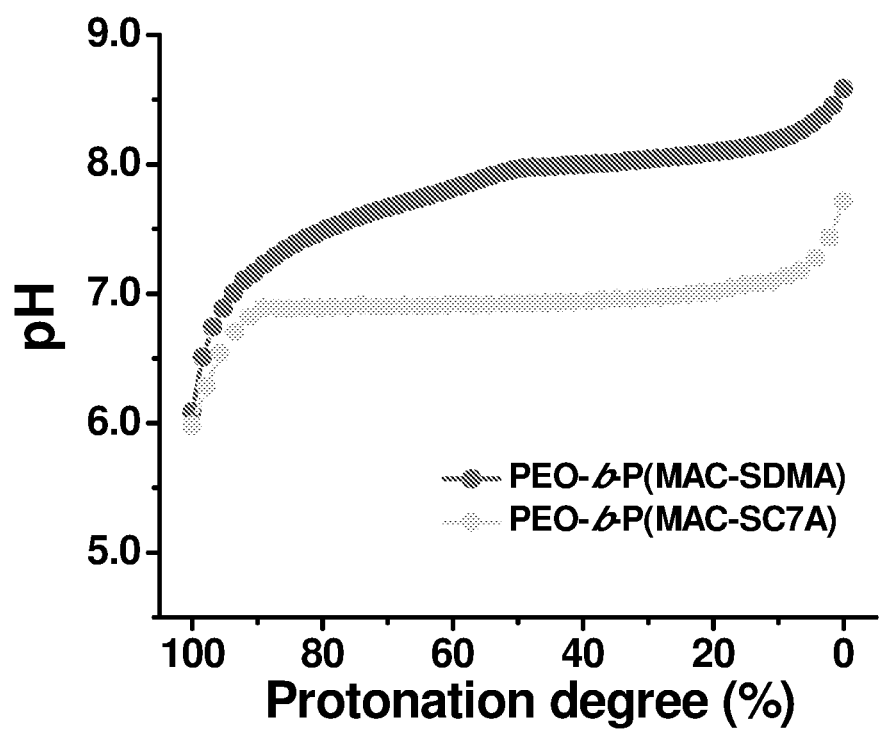
FIG. 4 shows pH changes as a function of protonation degree of $PEO_{123}$-b-$P(MAC-SDMA)_{135}$ and $PEO_{123}$-b-$P(MAC-SC7A)_{135}$.
Figure 19:
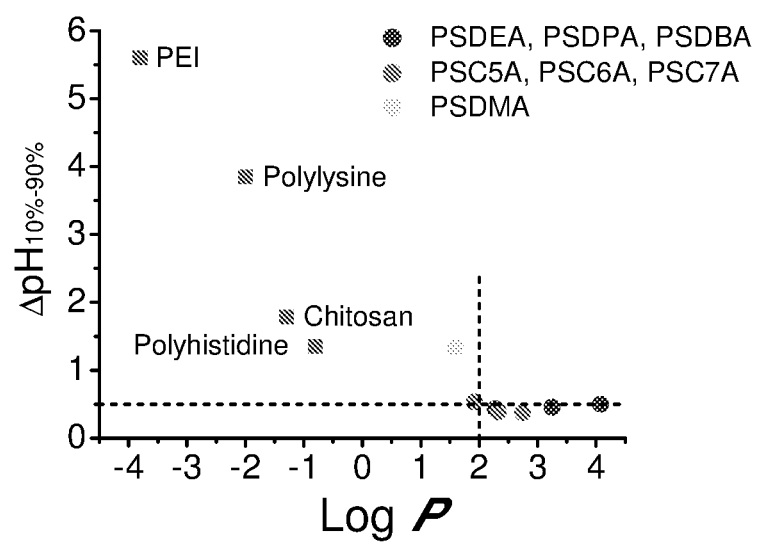
FIG. 19 shows pH transition sharpness ($\Delta pH_{10\%-90\%}$) as a function of log P of dUPS polymers. Commonly used polybases (poly(ethyleneimine), chitosan, polyhistidine, polylysine) are shown for comparison.

Results show that with the exception of $PEG_{123}$-b-P(MAC-SDMA)$_{135}$ (copolymer with the dimethyl amine side chain) (PSDMA), all the other copolymers displayed ultra-pH sensitive behaviors in the majority of the pH titration coordinate (FIG. 1A). The ultra-sensitive pH response is represented by the remarkable pH plateau across a broad range of protonation degrees, in particular from 10% to 90%, demonstrating the strong pH buffer effect within a narrow pH range. Interestingly, $PEO_{123}$-b-P(MAC-SDMA)$_{135}$ showed a two-segmented pH response with broad response above 50% protonation degree and narrow one below 50% (See FIG. 4). The $\Delta pH_{10\%-90\%}$ values were at or below 0.5 for these copolymers. For PSDMA with dimethyl amine side chains, a higher $\Delta pH_{10\%-90\%}$ value (1.2) was observed. Commonly used polybases (e.g., poly(ethyleneimine), chitosan, polyhistidine, polylysine) display broad pH responses with $\Delta pH_{10\%-90\%}>2$ (FIG. 19). (Li et al., 2016) Furthermore, the non-degradable PMMA copolymer with the dimethyl amine side chains displayed broad pH response throughout the whole pH titration coordinate (Li et al., 2016).

The apparent $pK_a$ values of the PEO-b-P(MAC-SR·HCl) copolymers showed an inverse correlation with the hydrophobicity of the tertiary amine substituents (FIG. 1B). The octanol-water partition coefficients (log P) of the repeating unit of the P(MAC-SR) segment (neutral/deprotonated state) was used to quantify the molecular hydrophobicity. Data shows a converged linear correlation of the apparent $pK_a$'s as a function of log P for copolymers containing either cyclic or linear amines. More hydrophobic side chains resulted in lower $pK_a$ values. The $pK_a$ values of these copolymers encompassed a broad range of physiological pH from 7.7 to 5.2.

The plot of $\Delta pH_{10\%-90\%}$ as a function of log P illustrates the presence of a hydrophobic threshold for the ultra-pH sensitive response (FIG. 1C). For copolymers with the log P>2, $\Delta pH_{10\%-90\%}$ values were at or below 0.5. For $PEO_{123}$-b-P(MAC-SDMA)$_{135}$ where the log P<2, a higher $\Delta pH_{10\%-90\%}$ value (1.2) was observed. For comparison, most commonly used polybases (e.g., poly(ethyleneimine), chitosan, polyhistidine, polylysine) are hydrophilic with log P<2 and display broad pH responses. Poly(ethyleneimine) had the highest $\Delta pH_{10\%-90\%}$ value (5.6) due to its strong hydrophilicity (log P=−3.8) and negative cooperativity in the protonation process. These results are consistent with the non-degradable PMMA polymers, suggesting molecular hydrophobicity is a common driver for the ultra-pH sensitivity in both systems (Li et al., 2016).

Figures 2A, 2B:
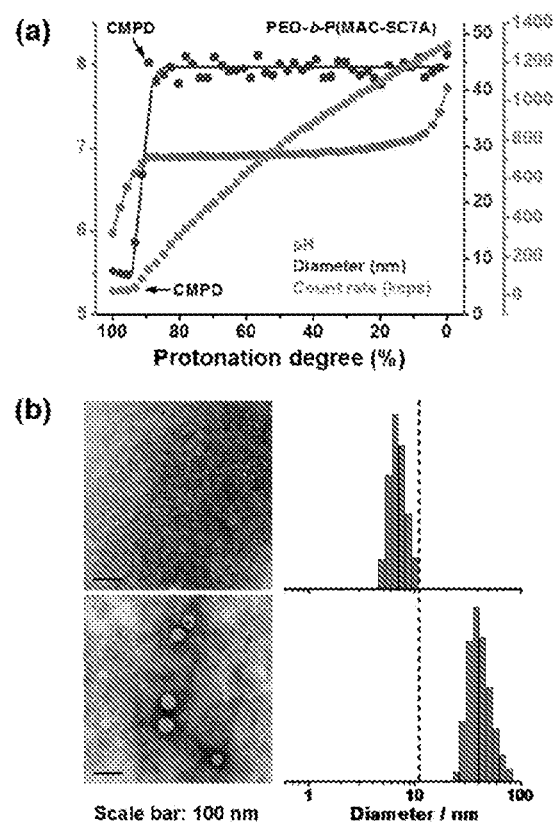
FIGS. 2A & 2B show the phase transition from a soluble unimer state to a micellar state drives the ultra-pH sensitive response of the copolymer.

The hydrophobicity-driven phase transition (i.e., micellization) and its influence on pH sensitivity for two copolymers, $PEO_{123}$-b-P(MAC-SC7A)$_{135}$ (PSC7A) and $PEO_{123}$-b-P(MAC-SDMA)$_{135}$ (PSDMA) was investigated with log P values above and below the hydrophobic threshold. For $PEO_{123}$-b-P(MAC-SC7A)$_{135}$, dynamic light scattering (DLS) results during pH titration (FIG. 2A) show that the polymer chains existed as unimers with hydrodynamic diameters below 10 nm when the protonation degree was above 90%. Micelles began to form when the protonation degree decreased to 90% and below as indicated by the increase in scattering count rates. The critical micellization protonation degree (CMPD) was defined as the protonation degree below which the polymer chains begin to self-assemble. For $PEO_{123}$-b-P(MAC-SC7A)$_{135}$, the CMPD value is 90%. Transmission electron microscopy (TEM) images and number-weighted hydrodynamic diameter distributions of $PEG_{123}$-b-P(MAC-SC7A)$_{135}$ at protonation degrees of 95% and 85% (FIG. 2B) further corroborated phase transitions across CMPD. Micelle diameters remained at approximately 45 nm with protonation degree below 90%.

Figures 5A, 5B:
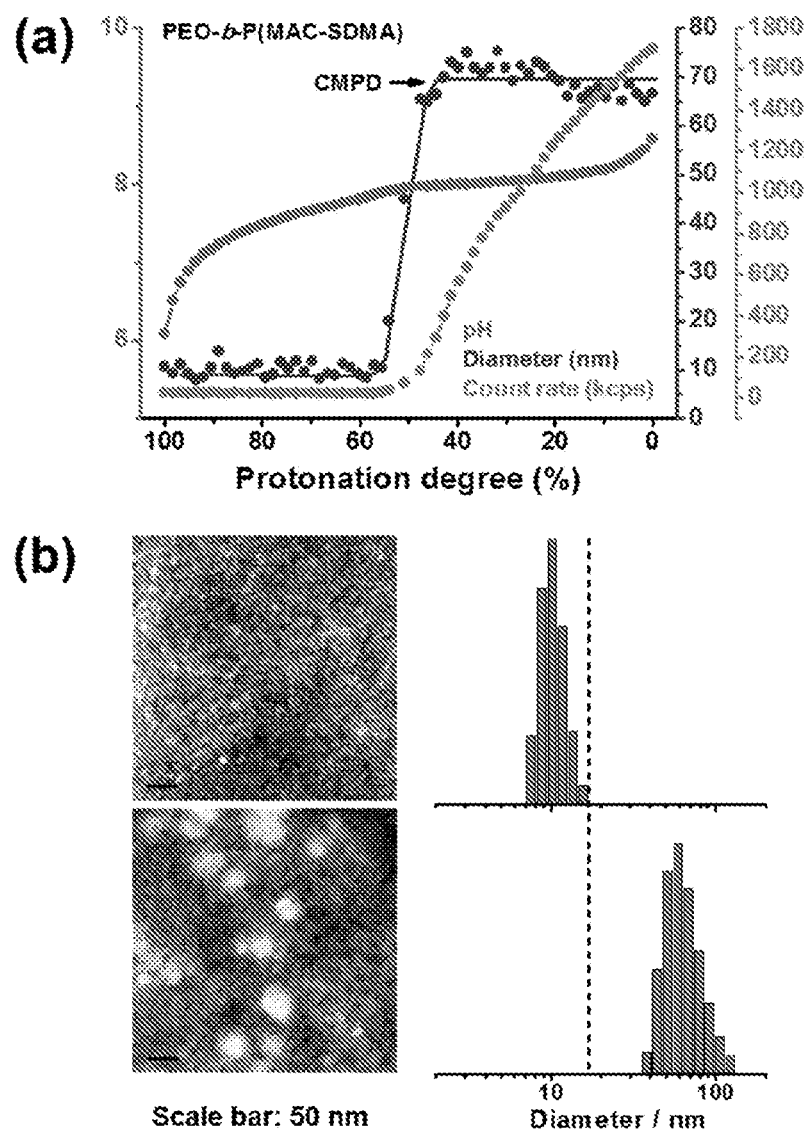
FIGS. 5A & 5B show (FIG. 5A) Number-weighted hydrodynamic diameters and light scattering count rates as a function of protonation degree during the pH titration of $PEG_{123}$-b-$P(MAC-SDMA)_{135}$ copolymer.
Figure 6:
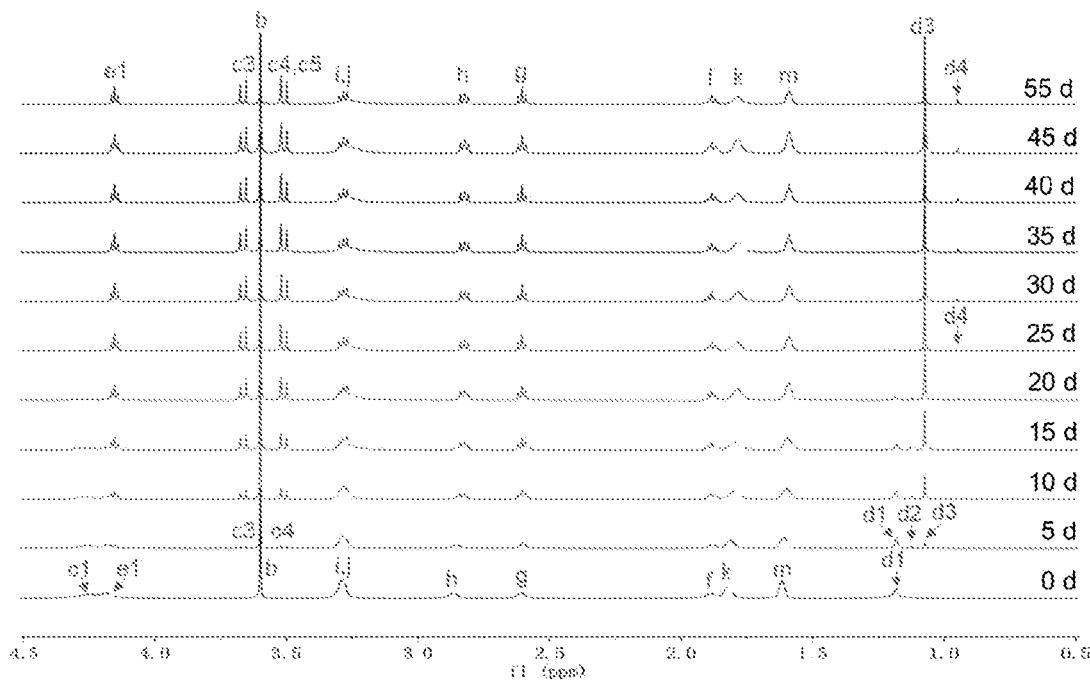
FIG. 6 shows the complete $^1$H NMR spectra of $PEO_{123}$-b-$P(MAC-SC7A)_{135}$ copolymer in pH 6.5 deuterated buffer solution over 55 days.
Figure 7:
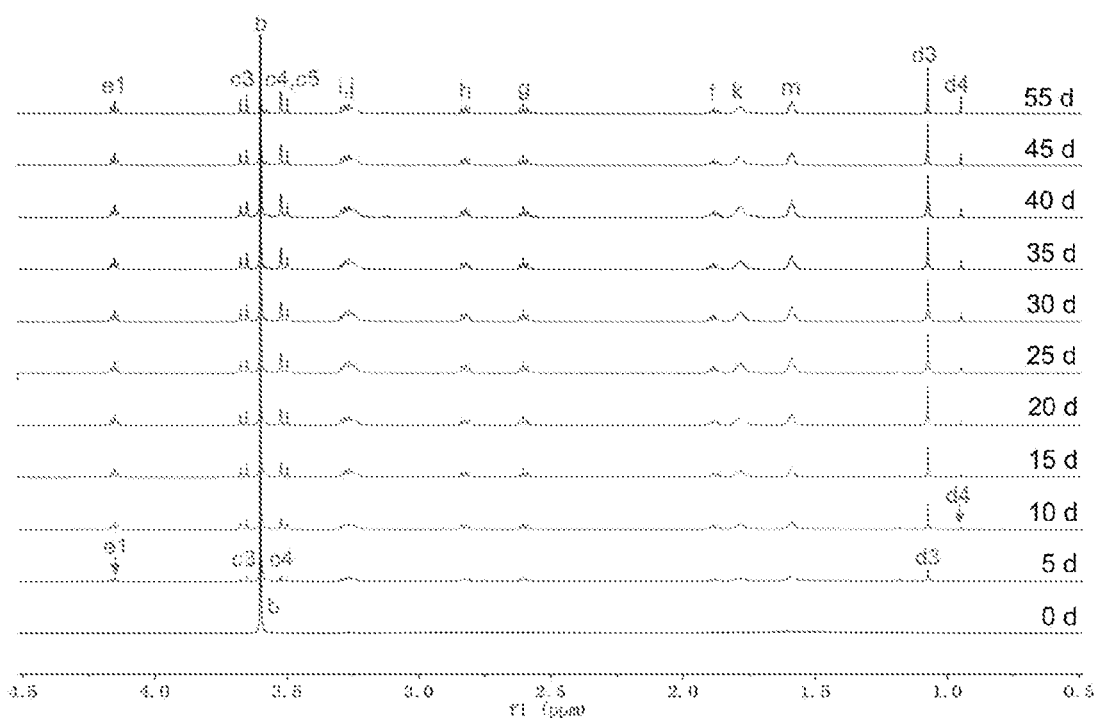
FIG. 7 shows the complete $^1$H NMR spectra of $PEO_{123}$-b-$P(MAC-SC7A)_{135}$ copolymer in pH 7.4 deuterated buffer solution over 55 days.

Micellization-induced ultra-pH sensitivity is more illustrative with $PEG_{123}$-b-P(MAC-SDMA)$_{135}$ (PSDMA). The polymer displays a two-segmented pH response with a broad response above 50% protonation degree and a narrow one below 50% (FIG. 5). Above 50% protonation degree, $PEG_{123}$-b-P(MAC-SDMA)$_{135}$ stayed as unimers and showed a broad pH response. Below 50% protonation, a dramatically sharpened pH response was observed. The ultra-pH sensitive response coincided with the formation of micelles across the CMPD, which allowed direct evidence of phase transition-induced ultra-pH sensitive response. Interestingly, the non-degradable PMMA polymers with the dimethyl amine side chains did not display any phase transition behaviors during the entire course of pH titration. These results suggest the polycarbonate backbone PMAC is more hydrophobic than PMMA and also contributes to the formation of micelles.

Figures 3A, 3B, 3C, 3D, 3E:
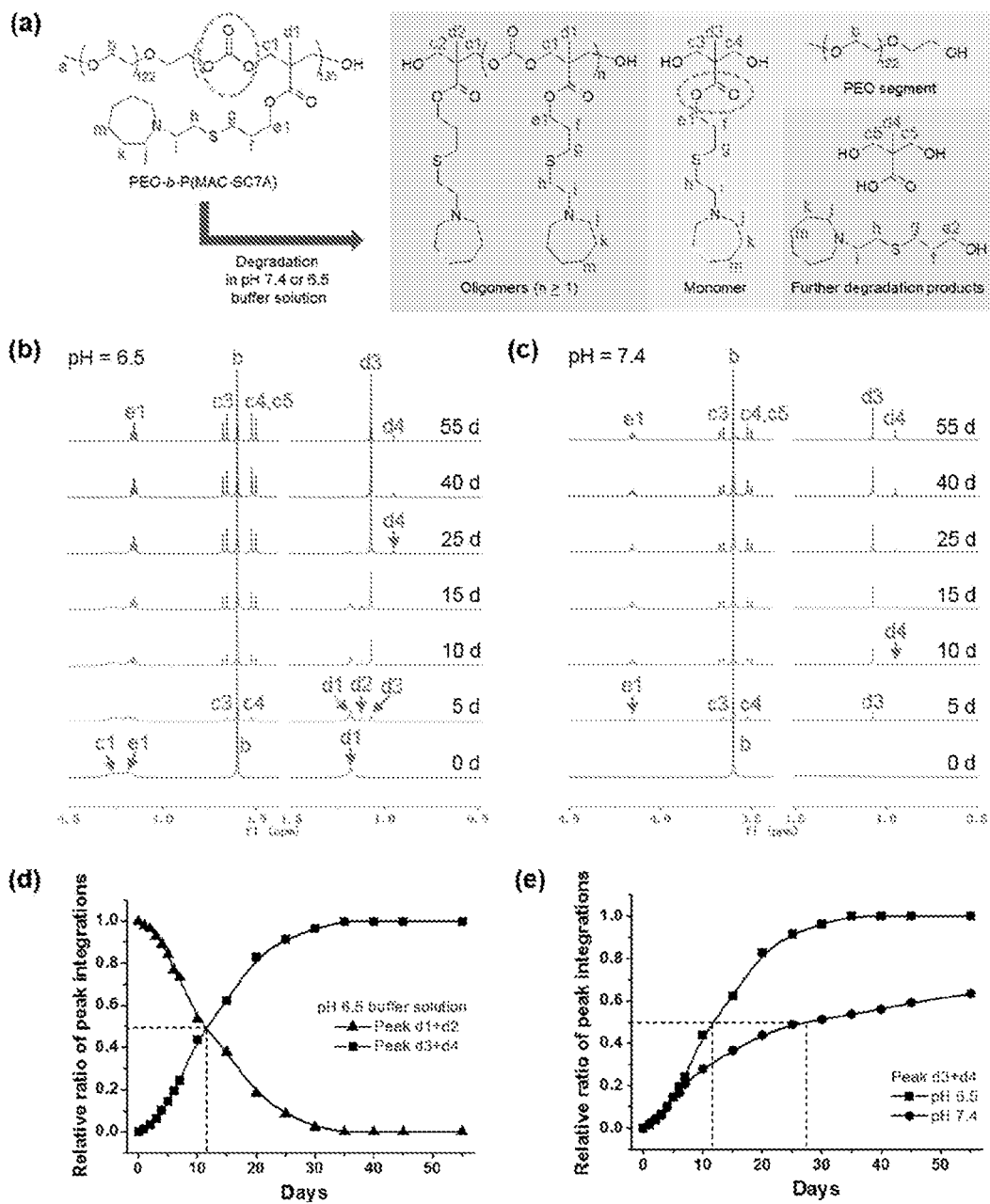
FIGS. 3A-3E show the degradation studies of $PEG_{123}$-b-$P(MAC-SC7A)_{135}$ copolymer in deuterated buffer solutions at pH 6.5 and 7.4.

$PEO_{123}$-b-P(MAC-SC7A)$_{135}$ was chosen as a representative biodegradable copolymer and investigated its degradation properties at pH 7.4 and 6.5 that mimic the normal physiological pH and early endosomal pH environments, respectively. The apparent $pK_a$ of $PEO_{123}$-b-P(MAC-SC7A)$_{135}$ is 6.9, thereby the copolymer exists either in the micelle or protonated unimer state at pH 7.4 and 6.5, respectively. The copolymer was prepared at 5.0 mg/mL in deuterated phosphate buffer solutions (50 mM) with NaCl (150 mM). NaOD or DCl solutions were added to adjust the pH to 6.5 or 7.4. FIG. 3A shows the structure of the $PEO_{123}$-b-P(MAC-SC7A)$_{135}$ copolymer and its degraded products. In the degradation process, the copolymer can degrade into oligomers, monomers, PEO segment, carbon dioxide, all due to the hydrolytic cleavage of the polycarbonate ester backbone (circle on the left structure in FIG. 3A). Further hydrolysis of the ester groups on the side chain (circle on the right structure in FIG. 3A) can lead to additional degradation products, 2,2-bis(hydroxymethyl) propionic acid (bis-HPA) and 3-(2-azepan-1-yl-ethyl sulfanyl)-propanol. $^1$H NMR was employed to monitor the formation of degradation products over 55 days in both pH solutions. Proton signal of PEO segment did not change over time, and its peak integration was used as an internal reference to the other proton peaks for quantification.

FIG. 3B shows the degradation profile of $PEG_{123}$-b-P$(MAC-SC7A)_{135}$ at pH 6.5 over time. Because the copolymer existed as protonated unimers in solution, all the proton peaks were visible at time zero (e.g., the protons signals corresponding to c1, d1 and e1). Within the first several days, new peaks (c3, c4, d2 and d3) formed and their intensity increased over time. On day 25, it appeared a majority of the copolymers degraded into monomeric structures (yellow panel in FIG. 3A) and PEO. Additional hydrolysis from day 25 to 55 shows a small percentage of further degradation product of bis-HPA (d4). Quantification of degradation kinetics was performed by analyzing the decrease of peak intensity of d1 and d2 (from polymer and oligomer states, respectively) or the increase of d3 and d4 (monomers and bis-HPA). Data shows simultaneous crossing of the two sets of curves at 50% of the relative peak intensity on day 12 (FIG. 3D). As used herein, $t_{1/2}$ is defined as the half-time for the conversion of 50% copolymers into monomers.

The degradation profile at pH 7.4 is more complex due to the formation of micelles. At time zero, only the PEO peak was visible by $^1$H NMR (FIG. 3C) because micelle formation of the P(MAC-SC7A) segment resulted in signal suppression due to fast transverse relaxation of the proton signals. Over time, proton signals from degraded monomers and bis-HPA were observed although with slower formation kinetics. Interestingly, on day 55, a higher ratio of bis-HPA to MAC monomer was found. Quantitative analysis of the monomer and bis-HPA peaks (d3+d4) showed a $t_{1/2}$ of 27 days in the higher pH environment (FIG. 3E). The slower degradation kinetics at pH 7.4 over 6.5 can be due to several factors, including the limited water penetration and access to PMAC because of hydrophobic micelle core, or reduced acid-catalyzed hydrolysis of carbonate bonds at pH 7.4.

The polycarbonate backbone is hydrolytically active, allowing the polymer to spontaneously degrade into biocompatible PEO segments and small molecules in aqueous environment. Degradation kinetics demonstrate that hydrolysis occurs at a slower rate at pH 7.4 than 6.5 ($t_{1/2}$ is at 27 and 12 d, respectively), likely due to the micellization of the PSC7A segment restricting water access to the carbonate groups at pH 7.4.

Example 3: Encapsulation of IL-2 Loaded Micelles

PEG-b-P(MAC-SDPA) (pKa=6.1) micelles were developed to deliver IL-2, a T cell growth factor to the tumor microenvironment. In a typical procedure, 0.2 mg PEG-b-P(MAC-SDPA) were dissolved in 0.05 mL methanol and then added into 0.5 mL PBS (pH 7.4) dropwise to form empty micelles. Methanol was removed by ultrafiltration (100 kDa, 5000 rpm/15 min for 2 times). The micelles are resuspended in PBS and then mixed with different amount of human recombinant IL-2 proteins.

The IL-2 loading efficiency was evaluated by mixing 20 µg (10%), 10 µg (5%), or 1 µg (0.5%) IL-2 with PEG-b-P(MAC-SDPA) micelles. Free IL-2 was removed from IL-2 loaded PEG-b-P(MAC-SDPA) micelles by ultrafiltration (100 kDa, 5000 rpm/15 min for 2 times). The filtrate was collected to determine IL-2 concentration by HPLC. It was found that over 90% IL-2 proteins were loaded inside PEG-b-P(MAC-SDPA) micelles in all cases. The IL-2 contents in PEG-b-P(MAC-SDPA) micelles were calculated to be 8.26%, 4.31% and 0.45%, respectively. The particle size of IL-2-PEG-b-P(MAC-SDPA) was about 55 nm as determined by dynamic light scattering analysis.

A. Evaluation of IL-2 Effect In Vitro

The IL-2 function was investigated using HEK-Blue™ IL-2 reporter cells, which are designed to monitor the activation of the JAK-STAT pathway induced by IL-2. Briefly, cells were rinsed by pre-warmed PBS and detached from the flask to prepare a cell suspension at ~280,000 cells/mL. Then 20 µL free IL-2 or IL-2 loaded PEG-b-P(MAC-SDPA) were added in to a flat-bottom 96-well plate. The samples were incubated with 180 µL of cell suspension per well at 37° C. in a $CO_2$ incubator (IL-2 concentration: 200, 50, 10, 2, 0.5, 0.2, 0.05, 0.01 ng/mL; PEG-b-P(MAC-SDPA) concentration: 40, 10, 2, 0.4, 0.1, 0.04, 0.01, 0.002 µg/mL). After 24 h, 20 µL of induced HEK-Blue™ IL-2 cell supernatant per well was added into another 96-well plate and mixed with 100 µL QUANTI-Blue™ detection solution. The plate was incubated at 37° C. incubator for 1 h and then SEAP levels were determined using a spectrophotometer at 630 nm.

Figure 8:
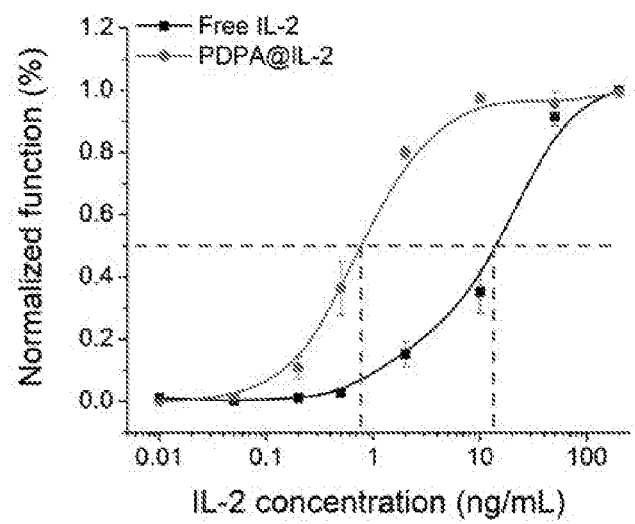
FIG. 8 shows normalized IL-2 function in vitro evaluated by HEK-Blue™ IL-2 reporter cells. IL-2 concentration: 200, 50, 10, 2, 0.5, 0.2, 0.05, 0.01 ng/mL; PEG-b-P(MAC-SDPA) concentration: 40, 10, 2, 0.4, 0.1, 0.04, 0.01, 0.002 µg/mL.

Data show that the biological effect of PEG-b-P(MAC-SDPA) encapsulated IL-2 was dramatically enhanced over free IL-2 (FIG. 8). The $EC_{50}$ of PEG-b-P(MAC-SDPA) encapsulated IL-2 and free IL-2 was 0.8 ng/mL and 15 ng/mL, respectively. Micelle delivered IL-2 displayed approximately 20 fold higher potency than free IL-2.

B. Evaluation of Anti-Tumor Efficacy In Vivo

The tumor growth inhibition effect of free IL-2 and PEG-b-P(MAC-SDPA)-IL-2 in a B16F10 melanoma tumor model was evaluated. C57bl/6j mice were first inoculated with B16F10 cells ($2.5 \times 10^5$ cells in 100 µL PBS). When tumors grew to 50-80 mm$^3$ in size, the mice were randomly divided into 5 groups. Free IL-2 or PEG-b-P(MAC-SDPA)-IL-2 were intratumorally or intravenously injected at day 1 and day 5 (IL-2: 1 µg per injection; PEG-b-P(MAC-SDPA): 200 µg per injection).

Figure 9:
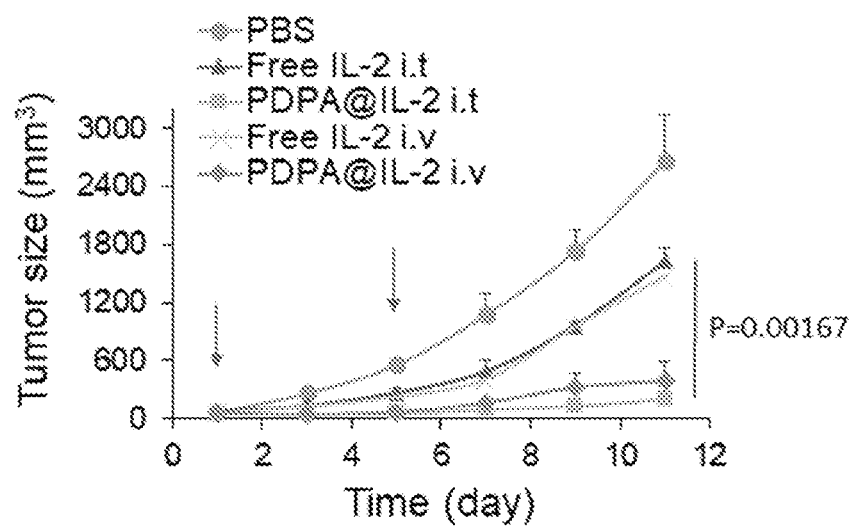
FIG. 9 shows B16F10 tumor growth curves under different treatment by IL-2 therapy. Free IL-2 or PEG-b-P(MAC-SDPA)-IL-2 were intratumorally or intravenously injected at day 1 and day 5 (IL-2: 1 µg per injection; PEG-b-P(MAC-SDPA): 200 µg per injection).

As shown in FIG. 9, PEG-b-P(MAC-SDPA)-IL-2 after i.v. injection exhibited an improved tumor growth suppression over i.v. injection of free IL-2 at the same dose. The anti-tumor effect of IL-2 after i.t injection was also enhanced after loaded in the PEG-b-P(MAC-SDPA) micelles over free IL-2. All the treated groups displayed tumor growth inhibition over the PBS control.

Figure 10:
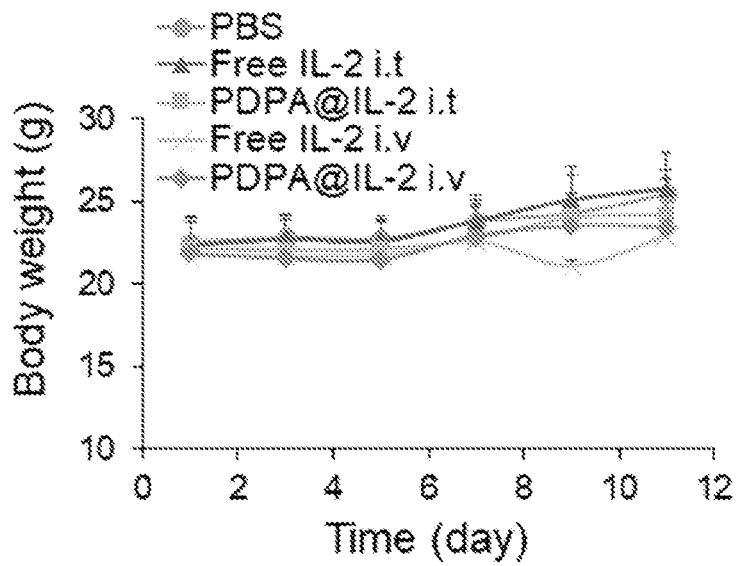
FIG. 10 shows body weight change curves within 11 days. Free IL-2 or PEG-b-P(MAC-SDPA)@IL-2 were intratumorally or intravenously injected at day 1 and day 5 (IL-2: 1 µg per injection; PEG-b-P(MAC-SDPA): 200 µg per injection).

The body weight of mice in PBS and free IL-2 i.t group slightly increased after one week likely due to the tumor growth. For PEG-b-P(MAC-SDPA)-IL-2 groups (both i.v and i.t), no obvious weight loss was found during therapy. However, after i.v injection, free IL-2 caused some temporal loss in mice (FIG. 10), indicating potential side effect from systemic administration of free IL-2.

Example 4: Encapsulation of cGAMP Micelles cGAMP is an endogenous second messenger and high-affinity ligand that triggers type I IFN production through the STING pathway. It is an anionic and highly water soluble molecule, where its activity and therapeutic efficacy are limited by its low bioavailability and poor drug-like properties. A nanoparticle was developed based on our biodegradable PEG-b-P(MAC-SC7A) micelles for efficient cytosolic delivery of cGAMP.

In a typical formulation process, PEG-b-P(MAC-SC7A·HCl) was first dissolved in 5% glucose aqueous solution to make the polymer concentration at 1.0 mg/mL. A small volume of HCl was then added, followed by the addition of different amounts of cGAMP (2%, 5% and 10% of polymer, w/w). The solution was added with specific volume of NaOH to adjust the final pH to ~7.4. After ultrafiltration (10 kDa), the filtrate was collected and the amount of unloaded cGAMP was measured by HPLC. The corresponding loading efficiency of cGAMP was calculated as:

Loading efficiency (%)=(weight of cGAMP loaded/
weight of total cGAMP)×100%.

Figure 11:
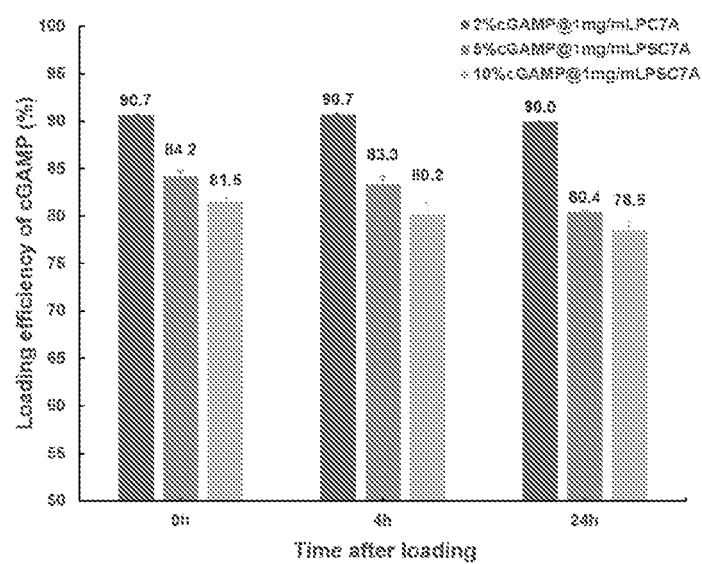
FIG. 11 shows loading efficiency of cGAMP in 1.0 mg/mL biodegradable PEG-b-P(MAC-SC7A) micelle nanoparticles.

The results are shown in FIG. 11. The loading efficiency of cGAMP in PEG-b-P(MAC-SC7A) nanoparticles can reach as high as 90% (2% cGAMP at 1.0 mg/mL PSC7A). The loading efficiency of the other two formulations also reach above 80%. This is very high for a cGAMP-loading nanoparticle formulation. Meanwhile, the formulation is very stable. The loading efficiency doesn't change much even after 24 h.

Example 5: STING Activation, Antigen Delivery, and T Cell Therapy of Cancer

Stimulator of interferon genes (STING) is an endoplasmic reticulum (ER)-bound homodimeric protein that plays a critical role in innate immunity (Barber, 2015; Ishikawa and Barber, 2008). STING activation leads to upregulation of type I interferons (IFNs), which enhance the $CD8^+$ T cell response against cancer (Baccala et al., 2007; Fuertes et al., 2013; Zitvogel et al., 2015). Previously, a non-degradable polymer nanoparticle, PC7A NP, have been reported that allows efficient encapsulation of tumor antigens and cytosolic delivery to lymph node-resident dendritic cells. The polymer also binds and activates STING and turns on the co-stimulatory pathways (CD80/CD86) for the generation of antigen-specific T cells (Luo et al., 2017).

In this study, the binding affinity of a series of dUPS copolymers (PSC7A, PSC6A, PSC5A and PSDEA) were first evaluated to the C-terminal domain of STING (139-397 AAs). pH 6.5 was chosen for the binding studies where all the copolymers stay as cationic unimers in solution. Isothermal calorimetry (ITC) results show that PSC7A copolymer had the highest binding affinity to STING with a dissociation constant ($K_d$) at 26 nM (FIG. 12A). The other two copolymers PSC6A and PSC5A with cyclic tertiary amines had less binding with $K_d$ values at 43 and 84 nM, respectively. The copolymer PSEDA with linear tertiary amines had negligible binding to STING. The $K_d$ value of non-degradable PC7A to STING is 72 nM, higher than that by the PSC7A. THP1-ISG cells were used to evaluate STING activation after treatment by different copolymers (0.5 µM) for 48 h (FIG. 12C). THP1-ISG cells were transfected by a luciferase reporter gene under the control of an interferon regulatory factor-inducible promoter. Upon STING activation, secretion of type I IFN will activate luciferase expression for luminescent detection. Results show IFN induction was elevated with dUPS copolymers with cyclic tertiary amines over the linear analogs. In particular, PSC7A copolymer resulted in a maximum of 14-fold increase in IFN induction, which correlated with the highest binding affinity to STING by the ITC measurement.

Figures 13A, 13B:
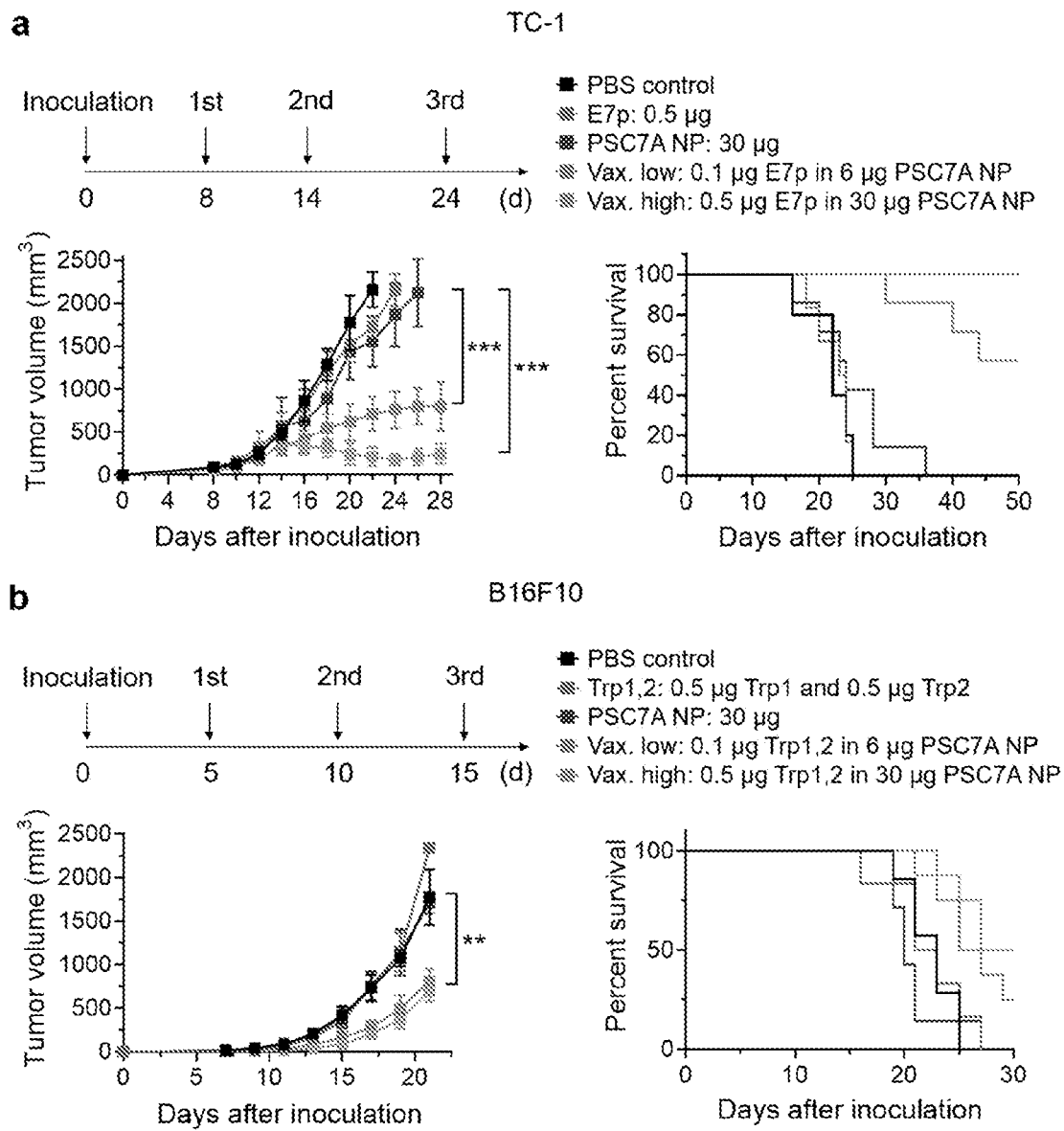
FIGS. 13A & 13B show PSC7A nanovaccine can inhibit tumor growth and prolong survival in tumor bearing mice. C57BL/6 mice (n=9 per group) inoculated with $2\times10^5$ FIG. 13A TC-1 or FIG. 13B B16-F10 melanoma cells were treated with PBS, tumor antigenic peptides only, PSC7A NP, low-dose PSC7A vaccine (Vax. low), or high-dose PSC7A vaccine (Vax. high) at specific time points, indicated above. Vaccination induced potent tumor growth inhibition and extended survival of these mice. For tumor growth studies, data are presented as means±s.e.m. and the statistical significance was calculated by t-test: *$P<0.001$, $P<0.01$, *$P<0.05$.
Figures 14A, 14B:
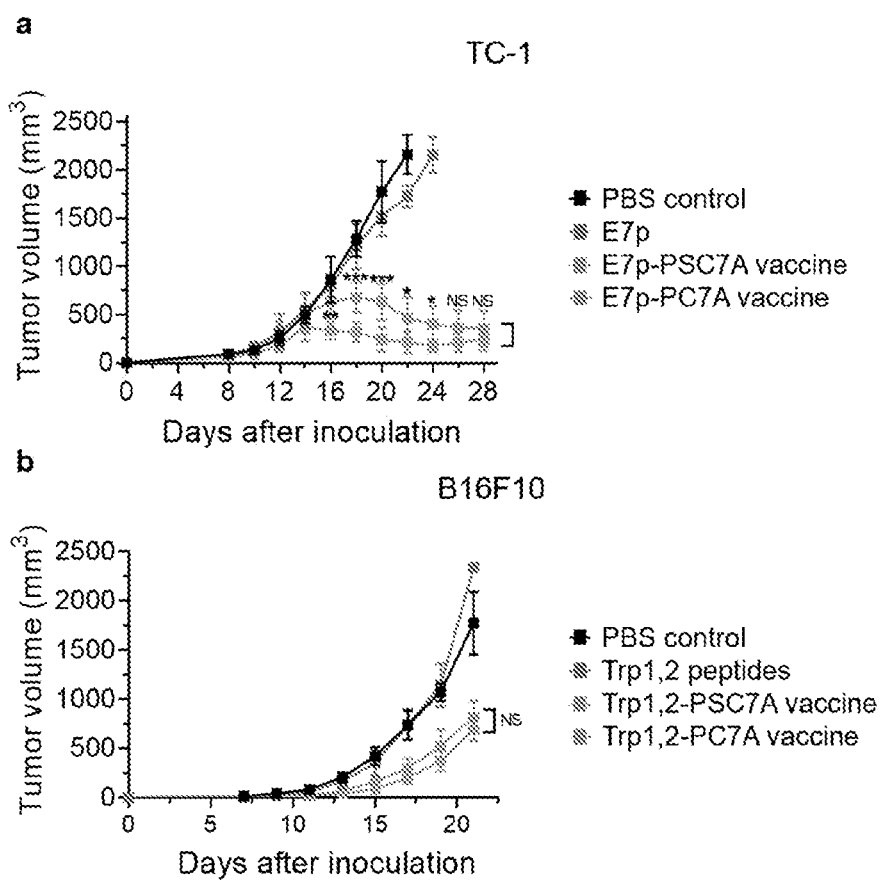
FIGS. 14A & 14B show PSC7A nanovaccines inhibit tumor growth in two animal tumor models. Non-degradable PC7A nanovaccines were used for comparison. C57BL/6 mice (n=9 per group) inoculated with $2\times10^5$ FIG. 14A TC-1 or FIG. 14B B16-F10 melanoma cells were treated with PBS, tumor antigenic peptides, PSC7A vaccine, or PC7A vaccine at specific time points. Data are presented as means±s.e.m. and the statistical significance was calculated by t-test: *$P<0.001$, $P<0.01$, *$P<0.05$.

Based on STING binding and activation assays, PSC7A copolymer were chose for the subsequent T cell vaccine studies (FIG. 13). PSC7A nanoparticles were first produced and then mixed with tumor-specific antigenic peptides. Human papilloma virus (HPV) E6/E7-transfected TC-1 and murine B16-F10 melanoma tumor models were used. Six- to eight-week-old C57BL/6 mice were first inoculated with tumor cells ($2\times10^5$) on the right thigh. In the TC-1 model, E7 peptide antigen (E7p, GQAEPDRAHYNIVTFCCKCD (SEQ. No. 1)) was used. Different groups were subcutaneously injected at the tail base on day 8, 16 and 24 after tumor inoculation (indicated in FIG. 13A). PBS, E7p and PSC7A NP only groups were used as controls. Results show that E7p and PSC7A NP only groups had marginal tumor growth inhibition response over the PBS control. Most of the animals were lost within 30 days after tumor inoculation. In contrast, the E7p-PSC7A NP groups led to dramatically improved tumor growth inhibition and prolonged survival. The low-dose PSC7A vaccine group (0.1 µg E7p in 6 µg PSC7A NP) resulted in >50% animal survival 50 days after tumor inoculation, whereas high-dose vaccine group (0.5 µg E7p in 30 µg PSC7A NP) had complete survival outcome (FIG. 13A). For the B16-F10 melanoma tumor model, a combination of tumor-associated antigens ($Trp1_{214-237}$ and $Trp2_{173-196}$) were loaded in PSC7A NPs. Peptide-PSC7A NP groups also displayed significantly improved tumor growth inhibition and prolonged survival over the PBS control and peptide or PSC7A NP only groups (FIG. 13B). In these two models, PSC7A nanovaccines showed slightly improved tumor inhibition in the TC-1 model and similar response in the B16F10 model compared to PC7A nanovaccines at the same dose (FIG. 14).

Results show dUPS polymers with cyclic amines exhibit stronger STING binding affinity and interferon induction than polymers with dialkyl amines, among which PSC7A is the most optimal. In vivo studies in two mouse tumor models show that antigen-loaded PSC7A NP can effectively produce antitumor immunity with significantly improved tumor growth inhibition and animal survival.

Example 6: Safety Evaluation of Nanoparticles Over Short and Long Term

Figure 16:
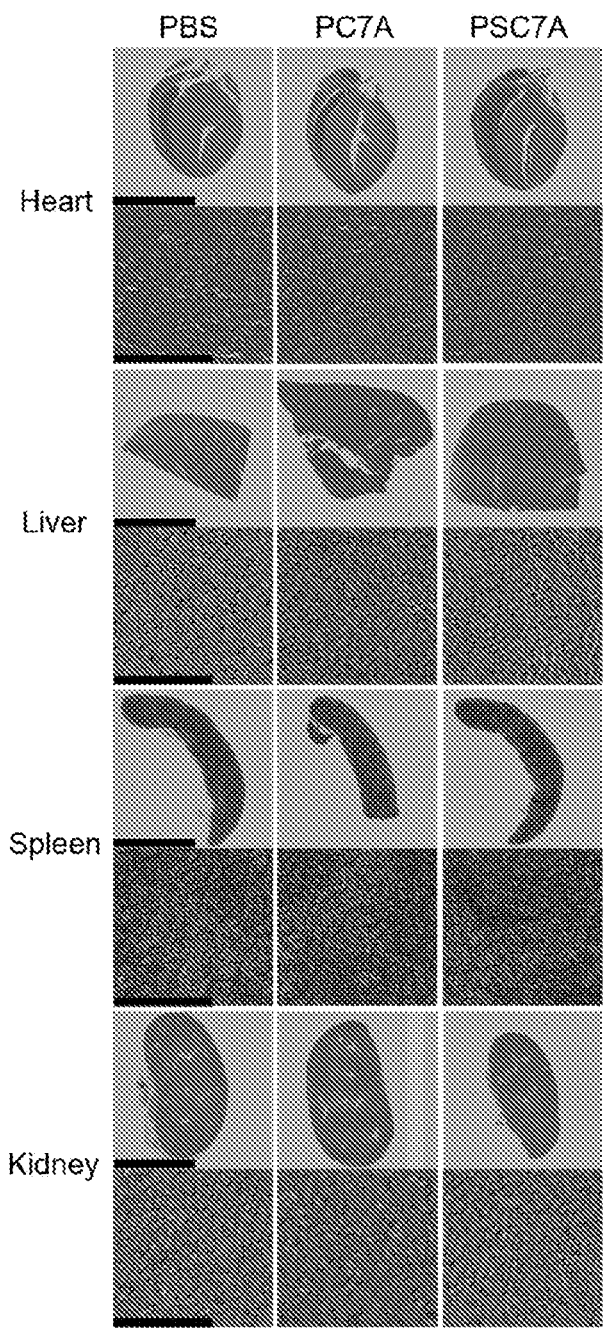
FIG. 16 shows histologic analysis of pivotal organs for short-term safety evaluation of PSC7A NP. Representative H&E sections of the organs from C57BL/6 mice after subcutaneous injection with PBS, 300 µg PSC7A NP or 300 µg PC7A NP on the right flank. Mice were executed and organs were collected 24 h after administration. Heart, liver, spleen and kidney histology were unremarkable after treatment by either polymer compared to PBS. For each organ group, scale bar: 5 mm (top) and 250 µm (bottom).

Particularly for polymers that actively engage the innate immune system through STING pathway, the safety indication is paramount for repeated administration during therapy. In this study, the dUPS PSC7A polymer, used for vaccination studies, were directly compared with its non-degradable PMMA based predecessor, PC7A (FIG. 15A). Six- to eight-week-old C57BL/6 mice were injected subcutaneously on their right flank with a high-dose of PSC7A NP or PC7A NP (300 µg, ten-fold of vaccine dose). Serum was collected 24 hours following the injection, and systemic inflammatory cytokine concentrations were determined. No obvious acute kidney or liver toxicity was observed 24 hours after treatment by either polymer (FIG. 15B). Generally, systemic cytokine expression was induced to a higher degree by PC7A NP than by PSC7A NP (FIG. 15C), indicating less systemic inflammatory response to the PSC7A NP. Histologic analysis of pivotal organs (heart, liver, spleen, and kidney) are unremarkable after treatment by either polymer compared to PBS (FIG. 16).

Figure 17:
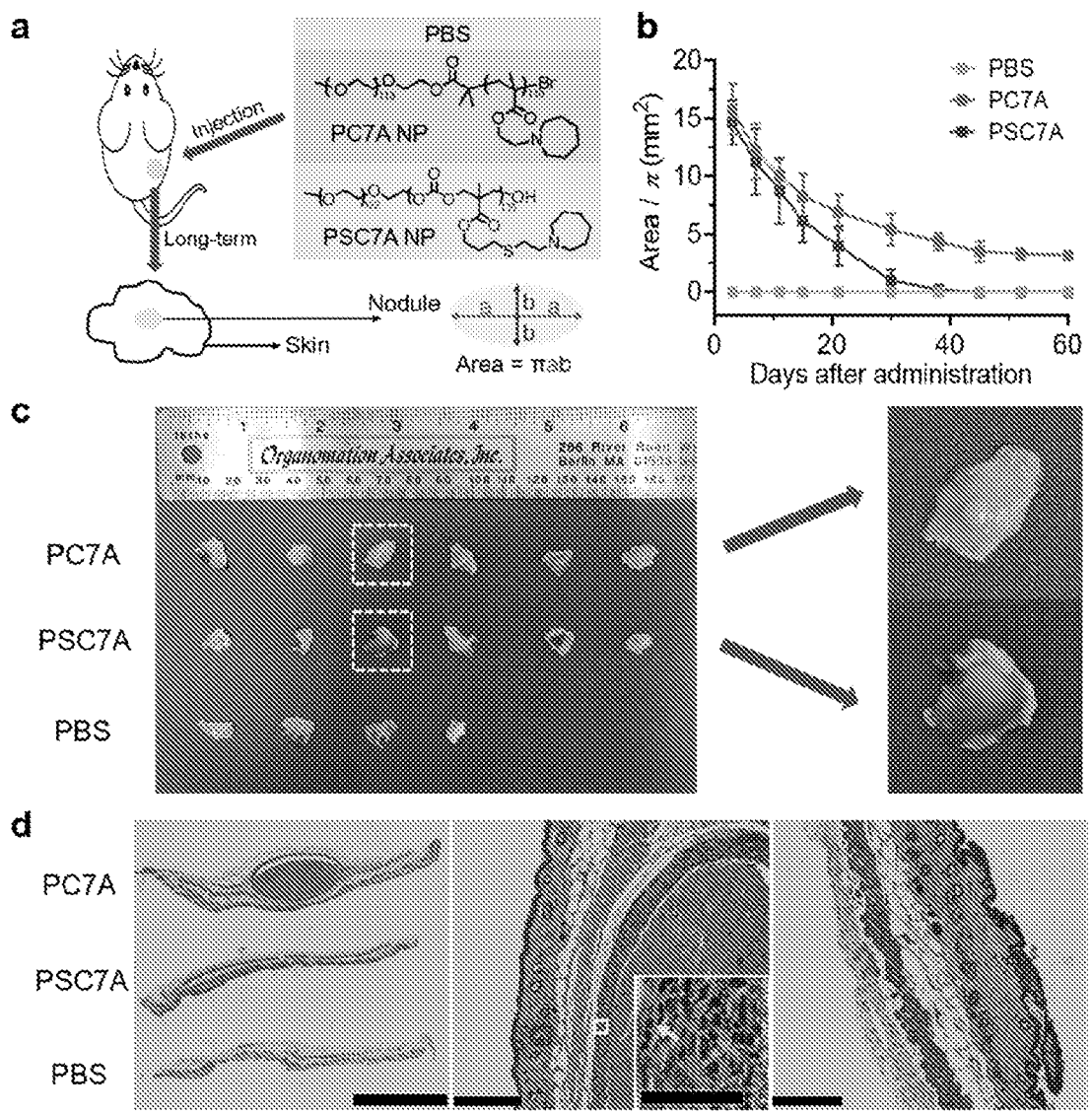
FIGS. 17A-17D show long-term safety evaluation of degradable PSC7A NP and non-degradable PC7A NP.
Figure 18:
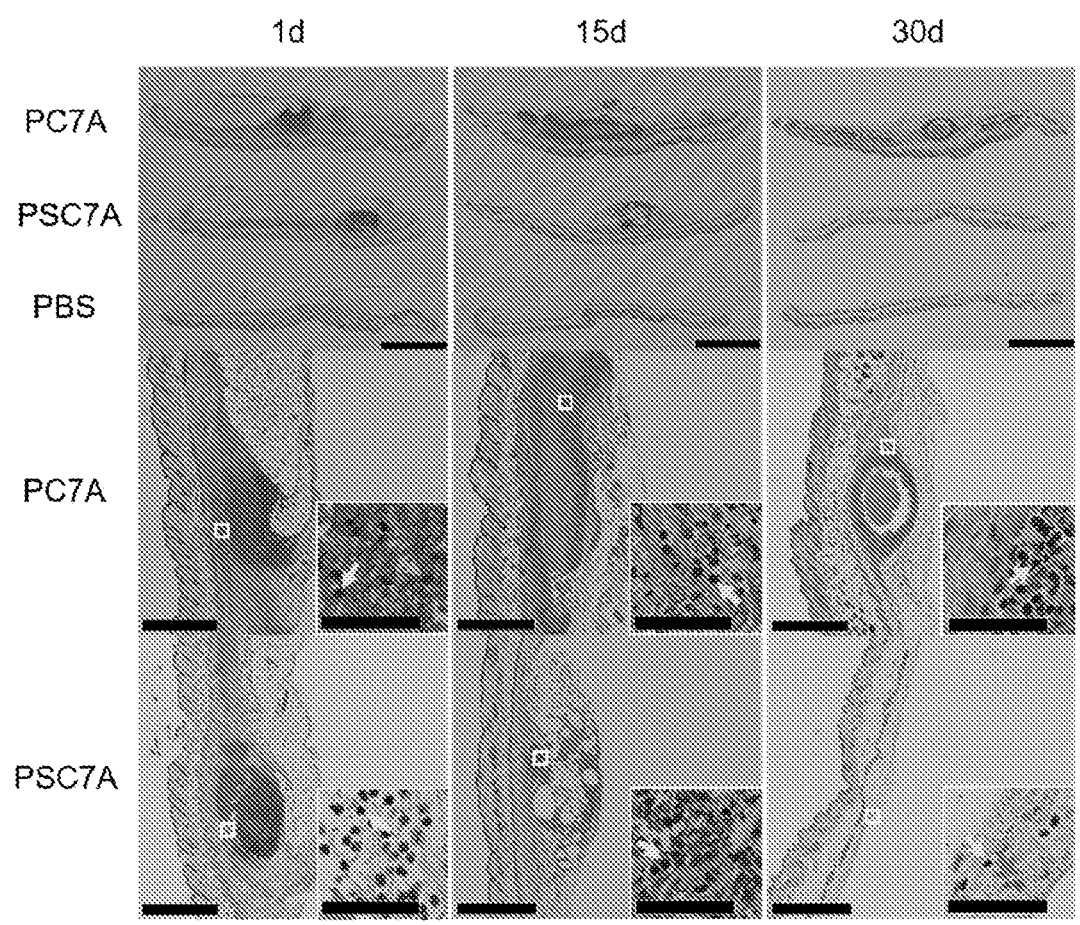
FIG. 18 shows histologic analysis of the skin tissues (injection sites) for long-term safety evaluation of PSC7A NP. Representative H&E sections of the skin tissues (injection sites) from C57BL/6 mice after subcutaneously injection with PBS, 300 µg PSC7A NP or 300 µg PC7A NP on the right flank. Mice were executed and the skin tissues were collected on day 1, 15 and 30 after administration. Inset: magnification of the area marked by a square. The dark gray, light grey, and medium grey arrows represent macrophages, lymphocytes and neutrophils, respectively. Scale bar: 2.5 mm (top), 1 mm (middle and bottom), 50 µm (inset).

The advantages of biodegradable PSC7A over non-degradable PC7A are more prominent in long-term safety studies. For this assay, mice were subcutaneously injected with PBS, 300 µg PSC7A NP, or 300 µg PC7A NP and observed over 60 days (FIG. 17A). The surface area of the resulting subcutaneous nodule was calculated based on an ellipse model to monitor progression (FIG. 17B). Within one day after administration, a large acute inflammatory reaction was observed at the injection site for both PC7A and PSC7A, likely due to innate immune stimulation. Histologically, abundant neutrophilic infiltration and necrotic debris were observed 24 hours after injection (day 1 time point, FIG. 18). Following this initial acute inflammatory reaction, the subcutaneous nodules reduced in size and gradually shifted into a chronic granulomatous inflammatory response, with more infiltration of macrophages and lymphocytes (day 15 and 30 time points, FIG. 18). PSC7A-induced nodules reduced in size at a faster rate than those induced by PC7A, indicating the PSC7A polymer was degrading and being excreted from the injection site, allowing eventual healing of the tissue. The half-time of PSC7A nodule size reduction is about 13 days, supporting the above chemical data for degradation kinetics. In contrast, the nodules induced by PC7A reduced in size over time until 45 days after administration, after which the nodules remained constant in size and appearance. On day 60, skin tissues at the injection site of all remaining mice were collected for histologic analysis (FIG. 17C). Grossly, 6/6 skin samples from the PC7A group contain a small, hard, yellow nodule. In contrast, none from the PSC7A group (0/6) contain nodules and resemble the PBS treated group in appearance. H&E staining on day 60 reveals nodules surrounded by granulomatous inflammation, with a "core/wall" appearance in mice treated with PC7A (FIG. 17D). Here, the "wall" is comprised mainly of macrophages with scattered lymphocytes and neutrophils, resulting from the acute and chronic innate stimulation and foreign-body reaction. The "core" is necrotic in nature, consisting mainly of the proteinaceous debris of dying cells, with some infiltrating macrophages, neutrophils, and lymphocytes. In contrast, skin tissues from mice treated with PSC7A demonstrate complete disappearance of any nodules and restoration to a healthy state by comparison with those treated by PBS.

In vivo safety studies show both PSC7A and PC7A induce a rapid, innate inflammatory response in the short-term with less systemic cytokine level from PSC7A NP than PC7A NP.

Long-term PSC7A degradation allows complete healing of the injection site while nodules surrounded by granulomatous inflammation persist in the PC7A site. Together, these data support complete degradation of PSC7A over time and a markedly improved safety profile compared to PC7A.

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Baccala et al., *Nat. Med.*, 13:543-551, 2007.
Barber, *Nat. Rev. Immunol.*, 15:760-770, 2015.
Blum et al., *J. Am. Chem. Soc.*, 137:2140-2154, 2015.
Casey et al., *Nat. Rev. Mol. Cell Bio.*, 11:50, 2009.
Fuertes et al., *Trends Immunol.*, 34:67-73, 2013.
Gerweck and Seetharaman, *Cancer Res.*, 56:1194, 1996.
Hao et al., *J. Am. Chem. Soc.*, 137:9206, 2015.
Hu et al., *J. Polym. Sci. Part A: Polym. Chem.*, 45:5518, 2007.
Huang et al., *Nat. Biomed. Eng.*, 2019.
Ishikawa and Barber, *Nature*, 455:674-678, 2008.
Luo et al., *Nat. Nanotech.*, 12:648, 2017.
Li et al., *Nat. Commun.*, 7:13214, 2016.
Moitra et al., *Angew. Chem.*, 126:1131-1135, 2013.
Moitra et al., *Angew. Chem. Int. Ed.*, 53:1113-1117, 2014.
Natarajan et al., *J. Org. Chem.*, 70:6362, 2005.
Reineke, *ACS Macro Lett.*, 5:14-18, 2016.
Torchilin, *Nat. Rev. Drug Discovery*, 13:813, 2014.
Wang et al., *Nat. Mater.*, 13:204, 2013.
Wang et al., *Nat. Commun.*, 6:8524, 2015.
Wang et al., *Angew. Chem. Int. Ed.*, 56:1319-1323, 2016.
Wang et al., *Adv. Drug Delivery Rev.*, 113:87-96, 2017.
Yang et al., *Adv. Drug Delivery Rev.*, 105:228-241, 2016.
Zhang et al., *ACS Macro Lett.*, 4:620-623, 2015.
Zhao et al., *Nat. Biomed. Eng.*, 1:0006, 2016.
Zhou et al., *Angew. Chem. Int. Ed.*, 50:6109-6114, 2011a
Zhou et al., *Angew. Chem.*, 123:6233-6238, 2011b
Zitvogel et al., *Nat. Rev. Immunol.*, 15:405-414, 2015.

What is claimed is:

1. A polymer of the formula:

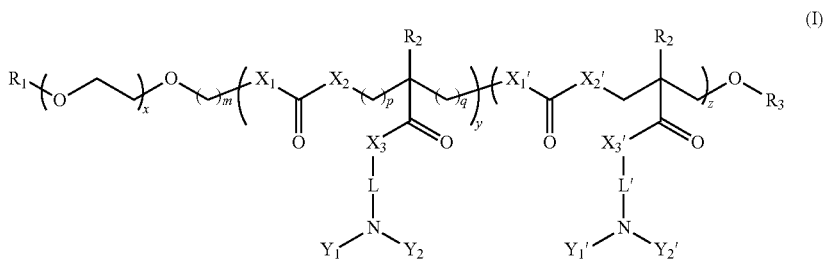

wherein:

$R_1$ is hydrogen, alkyl$_{(C\leq 8)}$, substituted alkyl$_{(C\leq 8)}$, or a thiol reactive group;

m is an integer from 1 to 8;

p and q are each independently 1, 2, or 3;

x is an integer from 10 to 200;

y is an integer from 20 to 200;

z is an integer from 0 to 200;

wherein the monomer of either y or z is randomly distributed in the polymer;

$X_1$, $X_2$, $X_1'$, and $X_2'$ are each independently O or $NR_a$, wherein:

$R_a$ is alkyl$_{(C\leq 6)}$ or substituted alkyl$_{(C\leq 6)}$;

$R_2$ and $R_2'$ are each independently hydrogen, alkyl$_{(C\leq 8)}$, or substituted alkyl$_{(C\leq 8)}$;

$R_3$ is hydrogen, alkyl$_{(C\leq 8)}$, or substituted alkyl$_{(C\leq 8)}$;

$X_3$ and $X_3'$ are each independently O or $NR_b$, wherein:

$R_b$ is hydrogen, alkyl$_{(C\leq 6)}$, or substituted alkyl$_{(C\leq 6)}$;

L and L' are each independently a group of the formula:

—$X_4$—$S(O)_n$—$X_5$— wherein:

n is 0, 1, or 2;

$X_4$ of L is —$CH_2CH_2$— and is attached via $X_3$; and $X_5$ of L is alkanediyl$_{(C\leq 8)}$ or substituted alkanediyl$_{(C\leq 8)}$; and $Y_1$, $Y_2$, $Y_1'$, and $Y_2'$ are each independently alkyl$_{(C\leq 12)}$, substituted alkyl$_{(C\leq 12)}$, alkenyl$_{(C\leq 12)}$, or substituted alkenyl$_{(C\leq 12)}$; or $Y_1$ and $Y_2$ or $Y_1'$ and $Y_2'$ are taken together and are alkanediyl$_{(C\leq 12)}$, alkenediyl$_{(C\leq 12)}$, or a substituted version of either group;

or a pharmaceutically acceptable salt thereof.

2. The polymer of claim 1 further defined as:

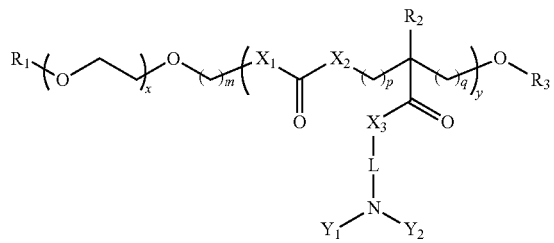

wherein:

$R_1$ is hydrogen, alkyl$_{(C\leq 8)}$, substituted alkyl$_{(C\leq 8)}$, or a thiol reactive group;

m is an integer from 1 to 8;

p and q are each independently 1, 2, or 3;

x is an integer from 10 to 200;

y is an integer from 20 to 200;

$X_1$ and $X_2$ are each O or $NR_a$, wherein:

$R_a$ is hydrogen, alkyl$_{(C\leq 6)}$, or substituted alkyl$_{(C\leq 6)}$;

$R_2$ is hydrogen, alkyl$_{(C\leq 8)}$, or substituted alkyl$_{(C\leq 8)}$;

$R_3$ is hydrogen, alkyl$_{(C\leq 8)}$, or substituted alkyl$_{(C\leq 8)}$;

$X_3$ is O or $NR_b$, wherein:

$R_b$ is hydrogen, alkyl$_{(C\leq 6)}$, or substituted alkyl$_{(C\leq 6)}$;

L is a group of the formula:

—$X_4$—$S(O)_n$—$X_5$— wherein:

n is 0, 1, or 2;

$X_4$ of L is —$CH_2CH_2$— and is attached via $X_3$; and $X_5$ of L is alkanediyl$_{(C\leq 8)}$ or substituted alkanediyl$_{(C\leq 8)}$; and $Y_1$ and $Y_2$ are each independently alkyl$_{(C\leq 12)}$, substituted alkyl$_{(C\leq 12)}$, alkenyl$_{(C\leq 12)}$, or substituted alkenyl$_{(C\leq 12)}$; or $Y_1$ and $Y_2$ are taken together and are alkanediyl$_{(C\leq 12)}$, alkenediyl$_{(C\leq 12)}$, or a substituted version of either group;

or a pharmaceutically acceptable salt thereof.

3. The polymer of claim 1, further defined as:

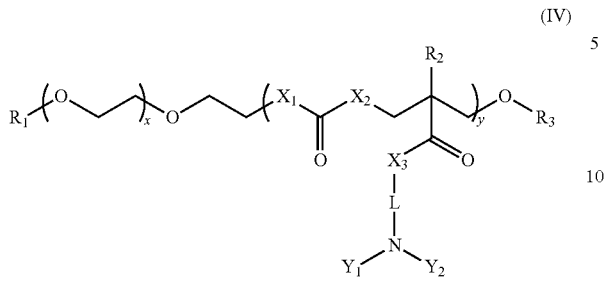

(IV)

wherein:
R₁ is hydrogen, alkyl$_{(C≤8)}$, substituted alkyl$_{(C≤8)}$, or a thiol reactive group;
m is an integer from 1 to 8;
x is an integer from 10 to 200;
y is an integer from 20 to 200;
X₁ and X₂ are each O or NR$_a$, wherein:
R$_a$ is hydrogen, alkyl$_{(C≤6)}$, or substituted alkyl$_{(C≤6)}$;
R₂ is hydrogen, alkyl$_{(C≤8)}$, or substituted alkyl$_{(C≤8)}$;
R₃ is hydrogen, alkyl$_{(C≤8)}$, or substituted alkyl$_{(C≤8)}$;
X₃ is O or NR$_b$, wherein:
R$_b$ is hydrogen, alkyl$_{(C≤6)}$, or substituted alkyl$_{(C≤6)}$;
L is a group of the formula:

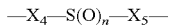
—X₄—S(O)$_n$—X₅— wherein:
n is 0, 1, or 2;
X₄ of L is —CH₂CH₂— and is attached via X₃; and
X₅ of L is alkanediyl$_{(C≤8)}$ or substituted alkanediyl$_{(C≤8)}$; and
Y₁ and Y₂ are each independently alkyl$_{(C≤12)}$, substituted alkyl$_{(C≤12)}$, alkenyl$_{(C≤12)}$, or substituted alkenyl$_{(C≤12)}$; or Y₁ and Y₂ are taken together and are alkanediyl$_{(C≤12)}$, alkenediyl$_{(C≤12)}$, or a substituted version of either group;
or a pharmaceutically acceptable salt thereof.

4. The polymer according to claim 1, further defined as:

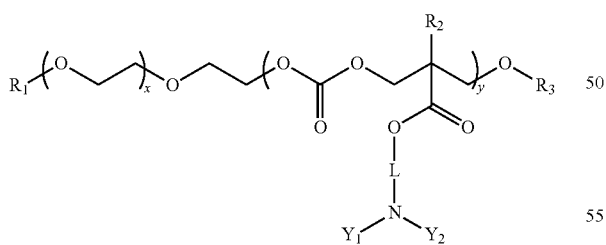

(V)

wherein:
R₁ is hydrogen, alkyl$_{(C≤8)}$, substituted alkyl$_{(C≤8)}$, or a thiol reactive group;
x is an integer from 10 to 200;
y is an integer from 20 to 200;
X₁ and X₂ are each O or NR$_a$, wherein:
R$_a$ is hydrogen, alkyl$_{(C≤6)}$, or substituted alkyl$_{(C≤6)}$;
R₂ is hydrogen, alkyl$_{(C≤8)}$, or substituted alkyl$_{(C≤8)}$;
R₃ is hydrogen, alkyl$_{(C≤8)}$, or substituted alkyl$_{(C≤8)}$;
X₃ is O or NR$_b$, wherein:
R$_b$ is hydrogen, alkyl$_{(C≤6)}$, or substituted alkyl$_{(C≤6)}$;
L is a group of the formula:

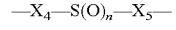
—X₄—S(O)$_n$—X₅— wherein:
n is 0, 1, or 2;
X₄ of L is —CH₂CH₂— and is attached via X₃; and
X₅ of L is alkanediyl$_{(C≤8)}$ or substituted alkanediyl$_{(C≤8)}$; and
Y₁ and Y₂ are each independently alkyl$_{(C≤12)}$, substituted alkyl$_{(C≤12)}$, alkenyl$_{(C≤12)}$, or substituted alkenyl$_{(C≤12)}$; or Y₁ and Y₂ are taken together and are alkanediyl$_{(C≤12)}$, alkenediyl$_{(C≤12)}$, or a substituted version of either group;
or a pharmaceutically acceptable salt thereof.

5. The polymer according to claim 1, further defined as:

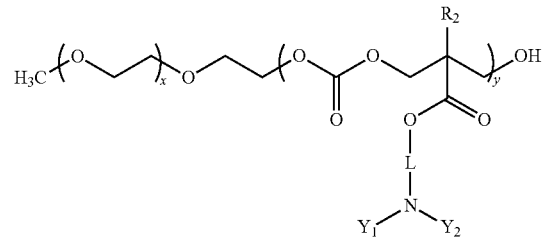

(VI)

wherein:
R₁ is hydrogen, alkyl$_{(C≤8)}$, substituted alkyl$_{(C≤8)}$, or a thiol reactive group;
x is an integer from 10 to 200;
y is an integer from 20 to 200;
R₂ is hydrogen, alkyl$_{(C≤8)}$, or substituted alkyl$_{(C≤8)}$;
R₃ is hydrogen, alkyl$_{(C≤8)}$, or substituted alkyl$_{(C≤8)}$;
L is a group of the formula:

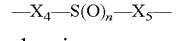
—X₄—S(O)$_n$—X₅— wherein:
n is 0, 1, or 2;
X₄ of L is —CH₂CH₂— and is attached via X₃; and
X₅ of L is alkanediyl$_{(C≤8)}$ or substituted alkanediyl$_{(C≤8)}$; and
Y₁ and Y₂ are each independently alkyl$_{(C≤12)}$, substituted alkyl$_{(C≤12)}$, alkenyl$_{(C≤12)}$, or substituted alkenyl$_{(C≤12)}$; or Y₁ and Y₂ are taken together and are alkanediyl$_{(C≤12)}$, alkenediyl$_{(C≤12)}$, or a substituted version of either group;
or a pharmaceutically acceptable salt thereof.

6. The polymer according to claim 1, further defined as:

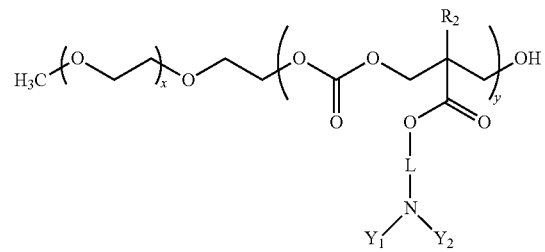

(VI)

wherein:
x is an integer from 10 to 200;
y is an integer from 20 to 200;
$R_2$ is hydrogen, alkyl$_{(C \leq 8)}$, or substituted alkyl$_{(C \leq 8)}$;
L is a group of the formula:

$$-X_4-S(O)_n-X_5-$$

wherein:
n is 0, 1, or 2;
$X_4$ of L is $-CH_2CH_2-$ and is attached via $X_3$; and
$X_5$ of L is alkanediyl$_{(C \leq 8)}$ or substituted alkanediyl$_{(C \leq 8)}$; and
$Y_1$ and $Y_2$ are each independently alkyl$_{(C \leq 12)}$, substituted alkyl$_{(C \leq 12)}$, alkenyl$_{(C \leq 12)}$, or substituted alkenyl$_{(C \leq 12)}$; or $Y_1$ and $Y_2$ are taken together and are alkanediyl$_{(C \leq 12)}$, alkenediyl$_{(C \leq 12)}$, or a substituted version of either group;

or a pharmaceutically acceptable salt thereof.

7. The polymer of claim 1, wherein $X_5$ of L is alkanediyl$_{(C \leq 6)}$.

8. The polymer of claim 7, wherein $X_5$ of L is $-CH_2CH_2-$.

9. The polymer according to claim 1, wherein $Y_1$ is alkyl$_{(C \leq 12)}$ or substituted alkyl$_{(C \leq 12)}$.

10. The polymer of claim 9, wherein $Y_1$ is alkyl$_{(C2-12)}$ or substituted alkyl$_{(C2-12)}$.

11. The polymer according to claim 1, wherein $Y_2$ is alkyl$_{(C \leq 12)}$ or substituted alkyl$_{(C \leq 12)}$.

12. The polymer according to claim 1, wherein $Y_1$ and $Y_2$ are taken together and are alkanediyl$_{(C \leq 12)}$ or substituted alkanediyl$_{(C \leq 12)}$.

13. The polymer of claim 12, wherein $Y_1$ and $Y_2$ are taken together and are $-CH_2CH_2CH_2CH_2-$, $-CH_2CH_2CH_2CH_2CH_2-$, or $-CH_2CH_2CH_2CH_2CH_2CH_2-$.

14. The polymer according to claim 1, wherein the polymer is further defined as:

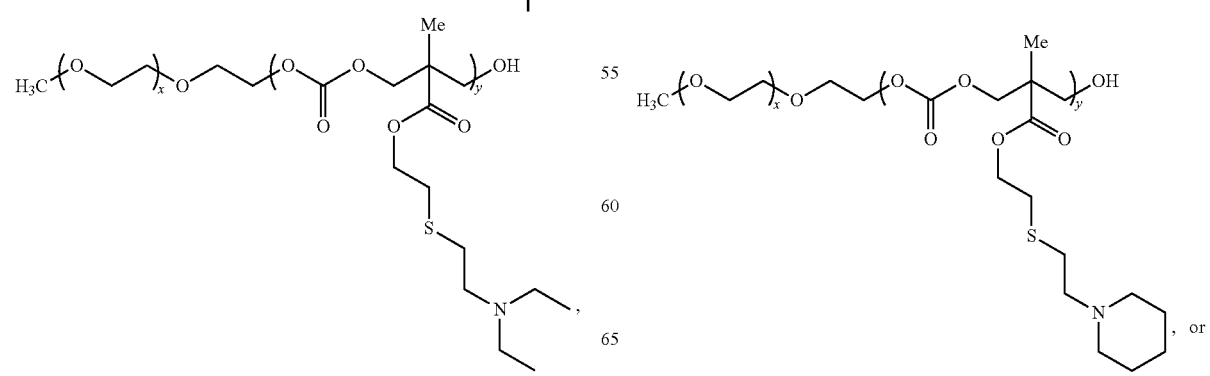

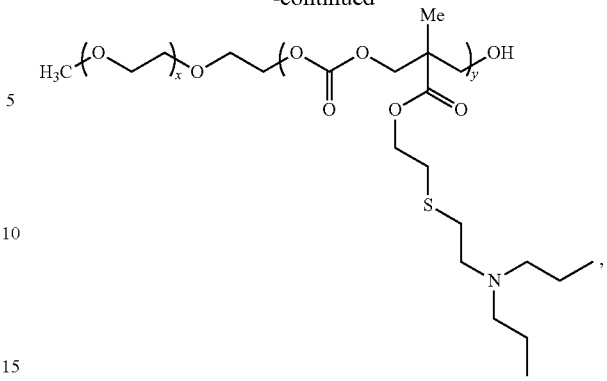

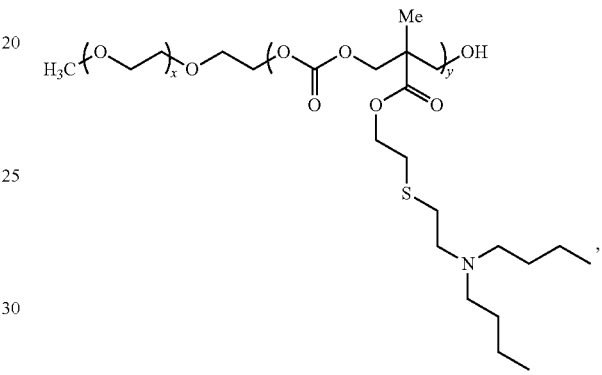

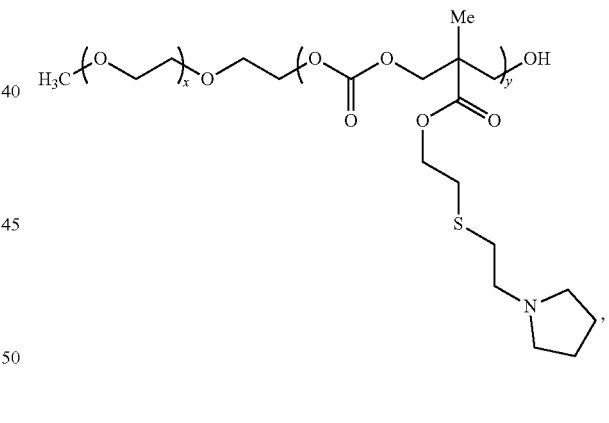

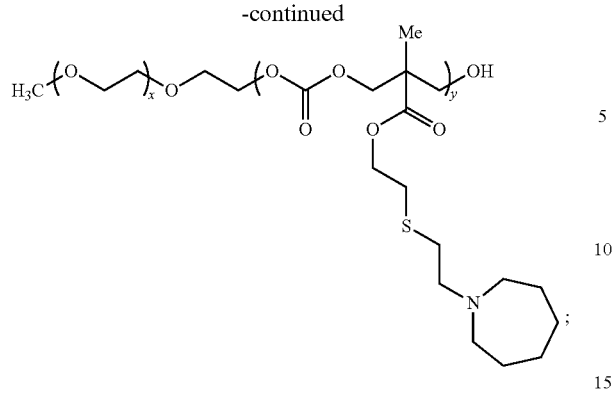
or a pharmaceutically acceptable salt thereof.
* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial sequence
<220> FEATURE:
<223> OTHER INFORMATION: Synthetic peptide
```

<400> SEQUENCE: 1

Gly Gln Ala Glu Pro Asp Arg Ala His Tyr Asn Ile Val Thr Phe Cys
1               5                   10                  15

Cys Lys Cys Asp
            20